(12) United States Patent
Subramaniam et al.

(10) Patent No.: US 12,194,451 B2
(45) Date of Patent: *Jan. 14, 2025

(54) BIMETAL-INCORPORATED MESOPOROUS SILICATES FOR ALCOHOL DEHYDRATION AND RELATED METHODS

(71) Applicant: University of Kansas, Lawrence, KS (US)

(72) Inventors: Bala Subramaniam, Lawrence, KS (US); Anand Ramanathan, Bartlesville, OK (US); Hongda Zhu, Lawrence, KS (US)

(73) Assignee: University of Kansas, Lawrence, KS (US)

( * ) Notice: Subject to any disclaimer, the term of this patent is extended or adjusted under 35 U.S.C. 154(b) by 1109 days.

This patent is subject to a terminal disclaimer.

(21) Appl. No.: 16/964,333

(22) PCT Filed: Jan. 24, 2019

(86) PCT No.: PCT/US2019/014901
§ 371 (c)(1),
(2) Date: Jul. 23, 2020

(87) PCT Pub. No.: WO2019/147770
PCT Pub. Date: Aug. 1, 2019

(65) Prior Publication Data
US 2021/0039077 A1   Feb. 11, 2021

Related U.S. Application Data

(60) Provisional application No. 62/621,691, filed on Jan. 25, 2018.

(51) Int. Cl.
| | | |
|---|---|---|
| *B01J 35/64* | (2024.01) | |
| *B01J 21/06* | (2006.01) | |
| *B01J 23/30* | (2006.01) | |
| *B01J 29/03* | (2006.01) | |
| *B01J 29/89* | (2006.01) | |
| *B01J 35/61* | (2024.01) | |
| *B01J 37/00* | (2006.01) | |
| *B01J 37/04* | (2006.01) | |
| *B01J 37/10* | (2006.01) | |
| *C07C 1/24* | (2006.01) | |
| *C07C 41/09* | (2006.01) | |

(52) U.S. Cl.
CPC ......... *B01J 35/647* (2024.01); *B01J 29/0341* (2013.01); *B01J 29/89* (2013.01); *B01J 35/615* (2024.01); *B01J 37/0018* (2013.01); *B01J 37/04* (2013.01); *B01J 37/10* (2013.01); *C07C 1/24* (2013.01); *C07C 41/09* (2013.01); *B01J 21/066* (2013.01); *B01J 23/30* (2013.01); *C01P 2006/16* (2013.01); *C07C 2529/89* (2013.01)

(58) Field of Classification Search
None
See application file for complete search history.

(56) References Cited

U.S. PATENT DOCUMENTS

| | | | |
|---|---|---|---|
| 8,299,310 B2 | 10/2012 | Zmierczak et al. | |
| 9,051,244 B2 | 6/2015 | Dhepe et al. | |
| 9,233,944 B2 | 1/2016 | Subramaniam et al. | |
| 9,994,601 B2 * | 6/2018 | Subramaniam | C07G 1/00 |
| 2012/0328500 A1 | 12/2012 | Larcher et al. | |
| 2017/0057903 A1 * | 3/2017 | Lin | B01J 29/0308 |
| 2017/0145043 A1 * | 5/2017 | Subramaniam | C07C 41/18 |
| 2018/0009725 A1 * | 1/2018 | Partington | C07C 1/24 |

OTHER PUBLICATIONS

Gobara ("Synthesis, Mechanisms and Different Applications of Mesoporous Materials Based on Silica and Alumina" Egypt. J. Chem., vol. 59, No. 2, 2016, pp. 163-194) (Year: 2016).*
Thanh Khoa Phung et al., "Conversion of ethanol over transition metal oxide catalysts: Effect of tungsta addition on catalytic behaviour of titania and zirconia," Applied Catalysis A: General, vol. 489, 2015; pp. 180-187.
V. L. Struzhko et al., Selectivity of Mesoporous Zirconium-Tungstate Oxide Systems in the Catalytic Conversion of Glycerin to Acrolein, Theoretical and Experimental Chemistry, vol. 49, No. 6, Jan. 2014; pp. 390-395.
Anand Ramanathan et al., "Niobium incorporated mesoporous silicate, Nb-KIT-6: Synthesis and characterization," Microporous and Mesoporous Materials, vol. 190, 2014; pp. 240-247.
Anand Ramanathan et al., "Direct incorporation of tungsten into ultra-large-pore three-dimensional mesoporous silicate framework: W-KIT-6," J. Porous Mater., 2012, vol. 19; pp. 961-968.
Hongda Zhu et al., "Effects of Tunable Acidity and Basicity of Nb-KIT-6 Catalysts on Ethanol Conversion: Experiments and Kinetic Modeling," AIChE Journal, Jul. 2017, vol. 63, No. 7; pp. 2888-2899.
The International Search Report and Written Opinion issued on Mar. 22, 2019 for International Patent Application No. PCT/US19/14901; pp. 1-10.
H. Zhu et al., "Positive Synergy in Bimetallic Wzr Mesoporous Silicates for Ethanol Conversion Reactions," Conference: AIChE Annual Meeting: Nov. 1, 2017. [online] Retrieved from the Internet<URL: https://www.alche.org/conferences/aiche-annual-meeting/2017/proceeding/paper/582ai-positive-synergy-bimetallic-wzr-mesoporous-silicates-ethanol-conversion-reactions>; abstract.

(Continued)

*Primary Examiner* — Rosalynd A Keys
(74) *Attorney, Agent, or Firm* — Bell & Manning, LLC

(57) ABSTRACT

Bimetal-incorporated mesoporous silicate catalysts are provided. In embodiments, such a catalyst comprises a silicate lattice, a first transition metal M, and a second transition metal M', wherein M and M' are selected from Zr, Nb, and W and are directly incorporated into the silicate lattice such that M and M' replace Si atoms. Methods of using the catalysts are also provided, including in methods for dehydrating alcohols. Methods of making the catalysts are also provided.

14 Claims, 13 Drawing Sheets

(56) References Cited

OTHER PUBLICATIONS

Celine Chizallet et al., "Pseudo-Bridging Silanols as Versatile Bronsted Acid Sites of Amorphous Aluminosilicate Surfaces," *Angew. Chem. Int. Ed.* 2009, vol. 48, pp. 2891-2893.

P. Schacht et al., "Upgrading of Heavy Crude Oil with W—Zr Catalyst," *Advances in Chemical Engineering and Science,* Apr. 1, 2014, vol. 4, No. 2, pp. 251, pp. 250-257.

Sudhakar Pichaikaran et al., "Rh/Ni wet-impregnated Ta3d mesostructured aluminosilicate and r-GO catalysts for hydrodeoxygenation of phenoxybenzene," New Journal of Chemistry, Jun. 12, 2017, vol. 41, No. 16; twelfth through thirteenth pages, 15 pages.

Hongda Zhu et al., "Genesis of Strong Bronsted Acid Sites in WZr-KIT-6 Catalysts and Enhancement of Ethanol Dehydration Activity," *ACS Catal.* Apr. 18, 2018, vol. 8, No. 6, pp. 4848-4859.

Hongda Zhu et al., "Exploiting the Tunable Acidity of Nb-KIT-6 Catalysts for Ethanol Dehydration: Experiments and Kinetic Modeling," presentation given at International Symposia on Chemical Reaction Engineering on Jun. 14, 2016 in Minneapolis, MN.

Hongda Zhu et al., "Remarkable Synergy of W and Zr Species in WZr-KIT-6 for Ethanol Dehydration," presentation given at AIChE meeting on Nov. 1, 2017 in Minneapolis, MN.

Tae Yong Kim et al., Preparation and characterization of mesoporous $Zr—WO_x/SiO_2$ catalysts for the esterification of 1-butanol with acetic acid, J. Mater. Chem., 2012, vol. 22, pp. 1-8.

Chelsey D. Baertsch et al., Genesis of Brønsted Acid Sites During Dehydration of 2-Butanol on Tungsten Oxide Catalysts. J. Catal. 2002, 205, 44-57.

Wu Zhou et al., "Nature of Catalytically Active Sites in the Supported WO3/ZrO2 Solid Acid System: A Current Perspective," *ACS Catal.* 2017, 7, 2181-2198.

Sha Li et al., "Formation of Subnanometer $Zr—WO_x$ Clusters within Mesoporous W—Zr Mixed Oxides as Strong Solid Acid Catalysts for Friedel-Crafts Alkylation," *J. Phys. Chem. C* 2014, 118, 6283-6290.

Oxana A. Kholdeeva et al., "$Zr_{IV}$-Monosubstituted Keggin-Type Dimeric Polyoxometalates: Synthesis, Characterization, Catalysis of $H_2O_2$ Based Oxidations, and Theoretical Study," *Inorg. Chem.* 2006, 45, 7224-7234.

Hugo Carabineiro et al., "Zirconium-Substituted Isopolytungstates: Structural Models for Zirconia-Supported Tungsten Catalysts.," *Inorg. Chem.* 2006, 45, 1915-1923.

Wu Zhou et al., "Identification of Active $Zr—WO_x$ Clusters on a $ZrO_2$ Support for Solid Acid Catalysts," *Nat. Chem.* 2009, 1, 722-728.

Joel B. Christian et al., "Structural Study of Ammonium Metatungstate," *J. Solid State Chem.* 2008, 181, 1782-1791.

Sadayuki Himeno et al., "Facile Preparation of an α-Keggin-Type $[H_3W_{12}O_{40}]_5$-complex: Does It Exist in Aqueous Solution?" Polyhedron 2010, 29, 2595-2599.

Ryan M. West et al., "Dehydration of Butanol to Butene over Solid Acid Catalysts in High Water Environments," *J. Catal.* 2009, 262, 134-143.

Guo Shiou Foo et al., "Role of Lewis and Brønsted Acid Sites in the Dehydration of Glycerol over Niobia," *ACS Catal.* 2014, 4, 3180-3192.

Nandiwale et al., Lignin Depolymerization into Aromatic Monomers over Acidic Mesoporous Silicates, Presentation at the 2016 AIChE Annual Meeting, San Francisco, CA, Nov. 16, 2016, 13 pages.

Nandiwale et al., Lignin Depolymerization into Aromatic Monomers over Novel Zirconium Incorporated Mesoporous Silicates, Poster at ISCRE 24 Foundations and Vistas of Chemical Reaction Engineering, Minneapolis, MN, Jun. 13, 2016.

Pineda et al., Heterogeneously catalyzed lignin depolymerization, Appl Petrochem Res, Jun. 3, 2016, 14 pages.

Liu et al., Catalytic Fast Pyrolysis of Lignocellulosic Biomass, Chemical Society Reviews 43, May 7, 2014, pp 1-53.

Deepa et al., Lignin Depolymerization into Aromatic Monomers over Solid Acid Catalysts, ACS Catal. 5, Dec. 1, 2014, pp. 365-379.

Kong et al., Direct Production of Naphthenes and Paraffins from Lignin, Chem. Commun., DOI: 10.1039/C5CC06828B., Sep. 28, 2015.

Anand Ramanathan et al., "Synthesis and characterization of Zirconium incorporated ultra large pore mesoporous silicate, Zr-KIT-6," Microporous and Mesoporous Materials 2013, vol. 167, pp. 207-212.

Anand Ramanathan et al., "Novel zirconium containing cage type silicate (Zr-KIT-5): An efficient Friedel-Crafts alkylation catalyst," Chemical Engineering Journal 2015, vol. 278, pp. 113-121.

Qing Pan et al., "Synthesis and Dehydration Activity of Novel Lewis Acidic Ordered Mesoporous Silicate: Zr-KIT-6," *Ind. Eng. Chem. Res.* 2013, vol. 52, pp. 15481-15487.

\* cited by examiner

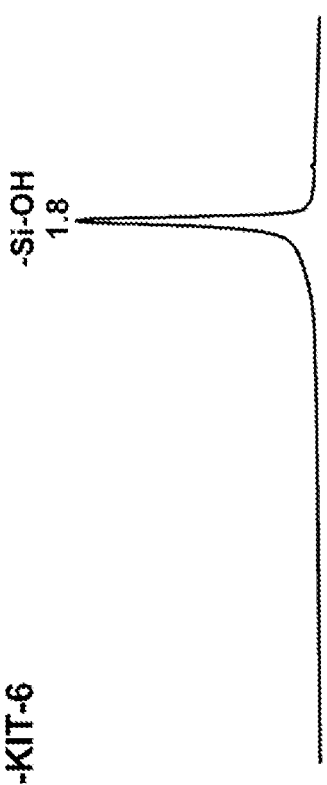
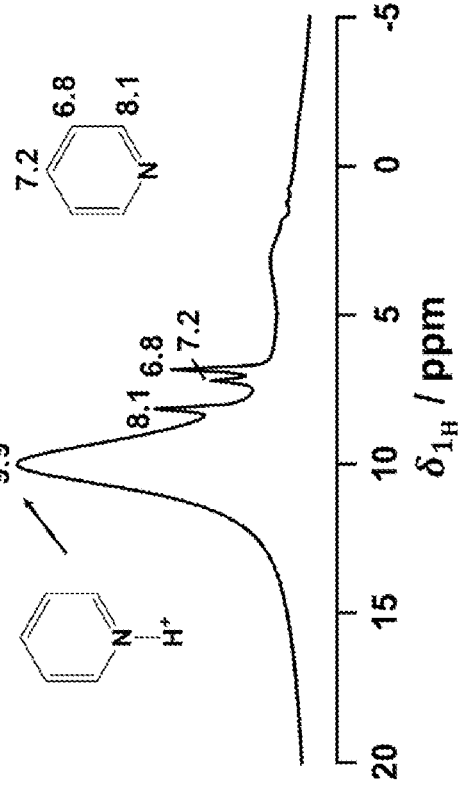
FIG. 2A
FIG. 2B

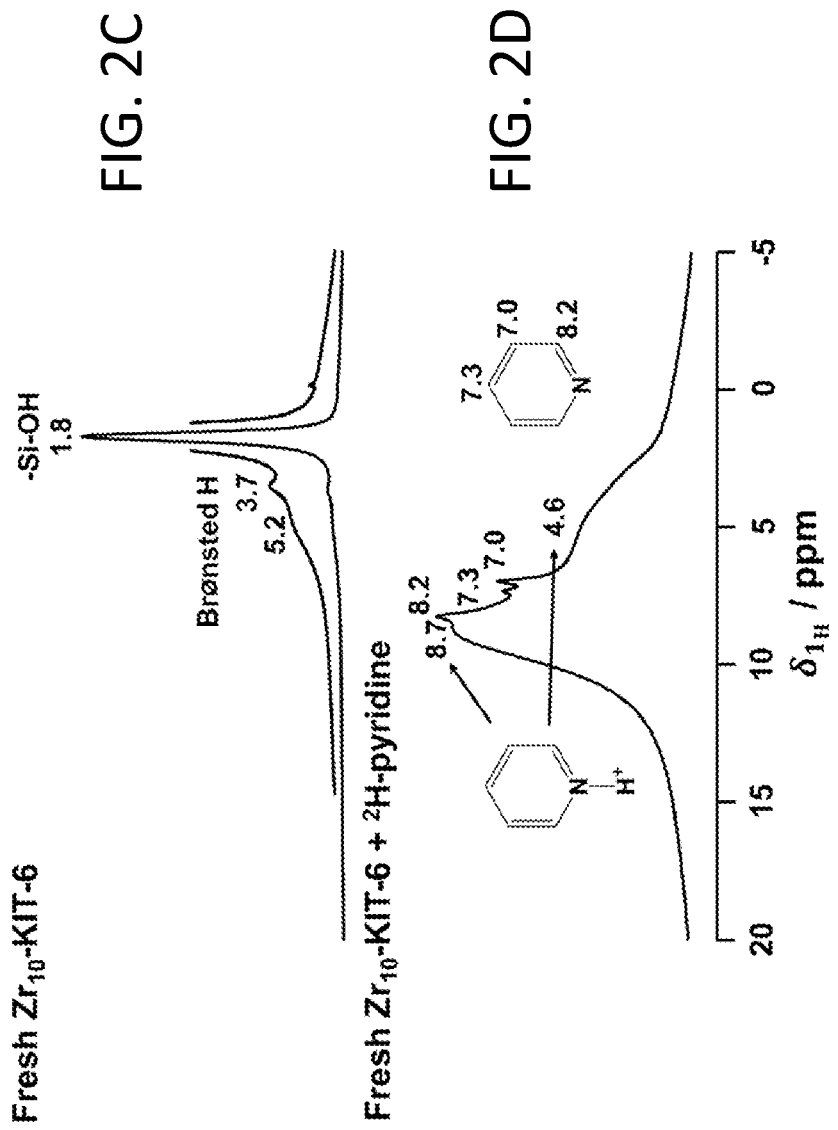

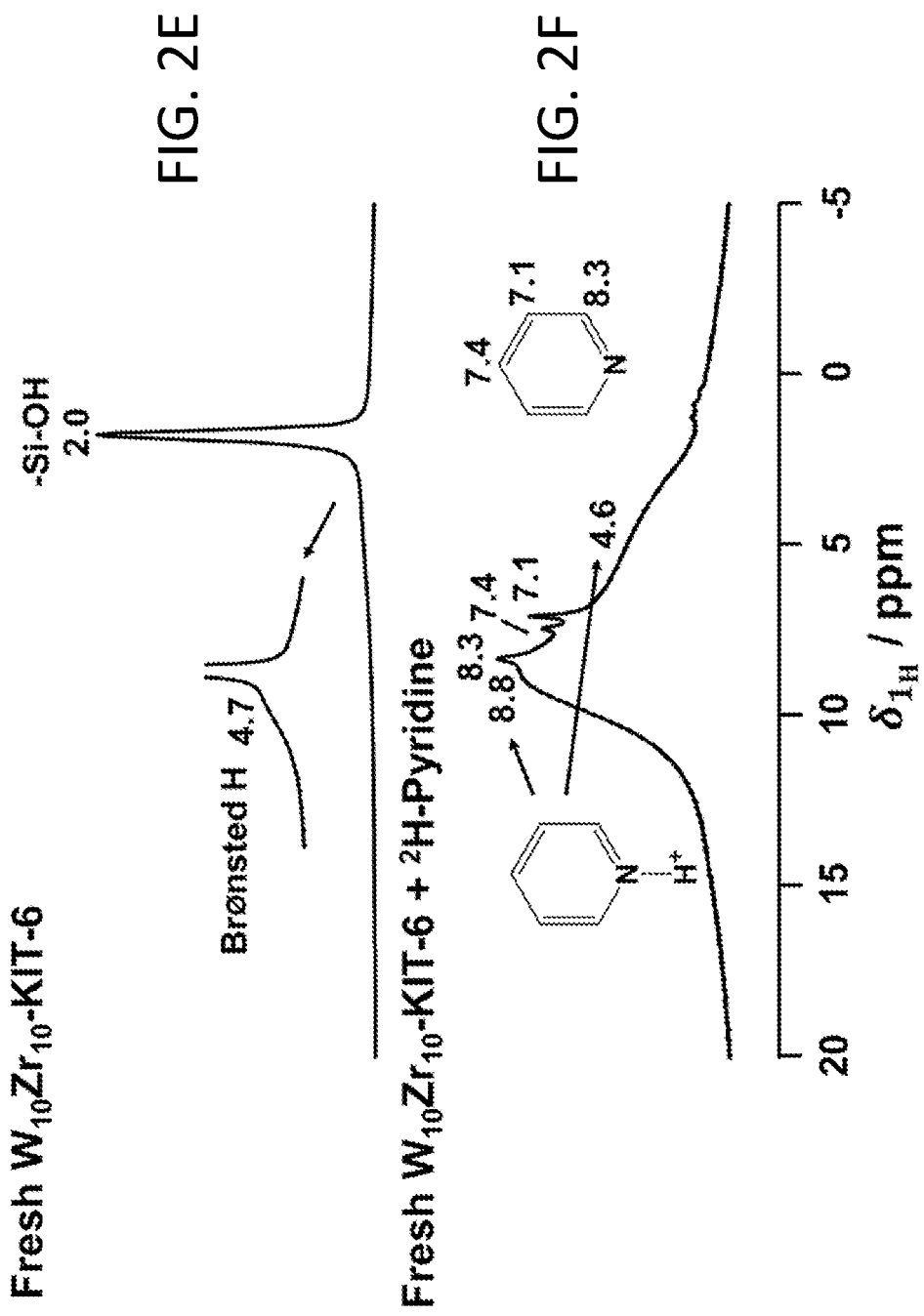

BIMETAL-INCORPORATED MESOPOROUS SILICATES FOR ALCOHOL DEHYDRATION AND RELATED METHODS

CROSS-REFERENCE TO RELATED APPLICATIONS

This application is a National Stage of International Application No. PCT/US2019/014901, filed Jan. 24, 2019, which claims the benefit of U.S. Patent Application No. 62/621,691, filed Jan. 25, 2018, the contents of which are herein incorporated by reference.

REFERENCE TO GOVERNMENT RIGHTS

This invention was made with government support under 2011-10006-30362 awarded by the United States Department of Agriculture. The government has certain rights in the invention.

BACKGROUND

Solid acid catalysts such as HZSM-5, mordenite, SAPO-34, and tungstated zirconia, have been extensively investigated for a variety of industrially significant reactions such as alcohol dehydration, alkylations and isomerization. A major drawback that hinders practical viability of microporous solid acid catalysts is rapid deactivation by fouling caused by coke deposits, although this fouling problem can be mitigated. The syntheses of catalysts such as Zr-KIT-6, Nb-KIT-6, and W-KIT-6 materials with enhanced pore accessibility for bulkier molecules has been reported. (See Pan, Q. et al., *Industrial & Engineering Chemistry Research* 2013, 52, 15481-15487; Ramanathan, A. et al., *Microporous and Mesoporous Materials* 2014, 190, 240-247; and Ramanathan, A. et al., *Journal of Porous Materials* 2012, 19, 961-968. However, none of these M-KIT-6 (M=Nb, W, Zr) materials exhibited ethanol dehydration activity comparable to either HZSM-5 or γ-$Al_2O_3$. (See Phung, T. K. et al., *Applied Catalysis A: General* 2015, 493, 77-89.; and Nash, C. P. et al., *Applied Catalysis A: General* 2016, 510, 110-124.

SUMMARY

Provided are bimetal-incorporated mesoporous silicate catalysts, methods of making the catalysts and methods of using the catalysts.

In one aspect, bimetal-incorporated mesoporous silicate catalysts are provided. In embodiments, such a catalyst comprises a silicate lattice, a first transition metal M, and a second transition metal M', wherein M and M' are selected from Zr, Nb, and W and are directly incorporated into the silicate lattice such that M and M' replace Si atoms.

In another aspect, methods of using bimetal-incorporated mesoporous silicate catalysts are provided. In embodiments, such a method involves dehydrating an alcohol, the method comprising exposing an alcohol to the bimetal-incorporated solid mesoporous silicate catalyst described immediately above, in a reactor under conditions sufficient to dehydrate the alcohol to one or more dehydration products.

In another aspect, methods of making bimetal-incorporated mesoporous silicate catalysts are provided. In embodiments, such a method comprises mixing a silicate precursor, a first transition metal precursor comprising M and a second transition metal precursor comprising M', with a structure directing composition comprising a structure directing agent and a co-solvent at a temperature and for a period of time; and subjecting the mixture to a hydrothermal treatment to form the bimetal-incorporated solid mesoporous silicate catalyst described immediately above.

In another embodiment, a method of making a bimetal-incorporated mesoporous silicate catalyst comprises exposing a coke-contaminated bimetal-incorporated mesoporous silicate catalyst to air at an elevated temperature and for a period of time, the catalyst comprising coke on its surface and a silicate lattice, a first transition metal M, and a second transition metal M', wherein M and M' are selected from Zr, Nb, and W and are directly incorporated into the silicate lattice such that M and M' replace Si atoms, to form a bimetal-incorporated mesoporous silicate catalyst comprising Brønsted acid sites having a strength greater than those of the coke-contaminated catalyst.

Other principal features and advantages of the disclosure will become apparent to those skilled in the art upon review of the following drawings, the detailed description, and the appended claims.

BRIEF DESCRIPTION OF THE DRAWINGS

Illustrative embodiments of the disclosure will hereafter be described with reference to the accompanying drawings.

FIGS. 2A-2F show $^1H$ MAS spectra of fresh and pyridine-adsorbed catalyst samples: Fresh $W_{10}$-KIT-6 (FIG. 2A), fresh $W_{10}$-KIT-6+$^2H$-pyridine (FIG. 2B), fresh $Zr_{10}$-KIT-6 (FIG. 2C), fresh $Zr_{10}$-KIT-6+$^2H$-pyridine (FIG. 2D), fresh $W_{10}Zr_{10}$-KIT-6 (FIG. 2E), fresh $W_{10}Zr_{10}$-KIT-6+$^2H$-pyridine (FIG. 2F).

FIG. 8A shows fresh, spent and air-regenerated samples analyzed in air flow and FIG. 8B shows spent sample analyzed sequentially in nitrogen flow and air flow.

DETAILED DESCRIPTION

Provided are bimetal-incorporated mesoporous silicate catalysts, methods of making the catalysts and methods of using the catalysts.

The bimetal-incorporated mesoporous silicate catalysts may be used in alcohol dehydration reactions and other reactions to provide a variety of value added chemicals. An embodiment of a method of dehydrating an alcohol comprises exposing an alcohol to a bimetal-incorporated mesoporous silicate catalyst under conditions sufficient to dehydrate the alcohol to form one or more dehydration products. At least some embodiments of the dehydration method exhibit one or more advantages such as high alcohol conversion, high selectivity towards specific dehydration products, and reduced steric hindrance towards bulky molecules. Moreover, the present dehydration methods employ mild conditions (low temperature and atmospheric pressure) and the present bimetal-incorporated mesoporous silicate catalysts are environmental friendly (non-toxic and non-corrosive).

Figure 4:
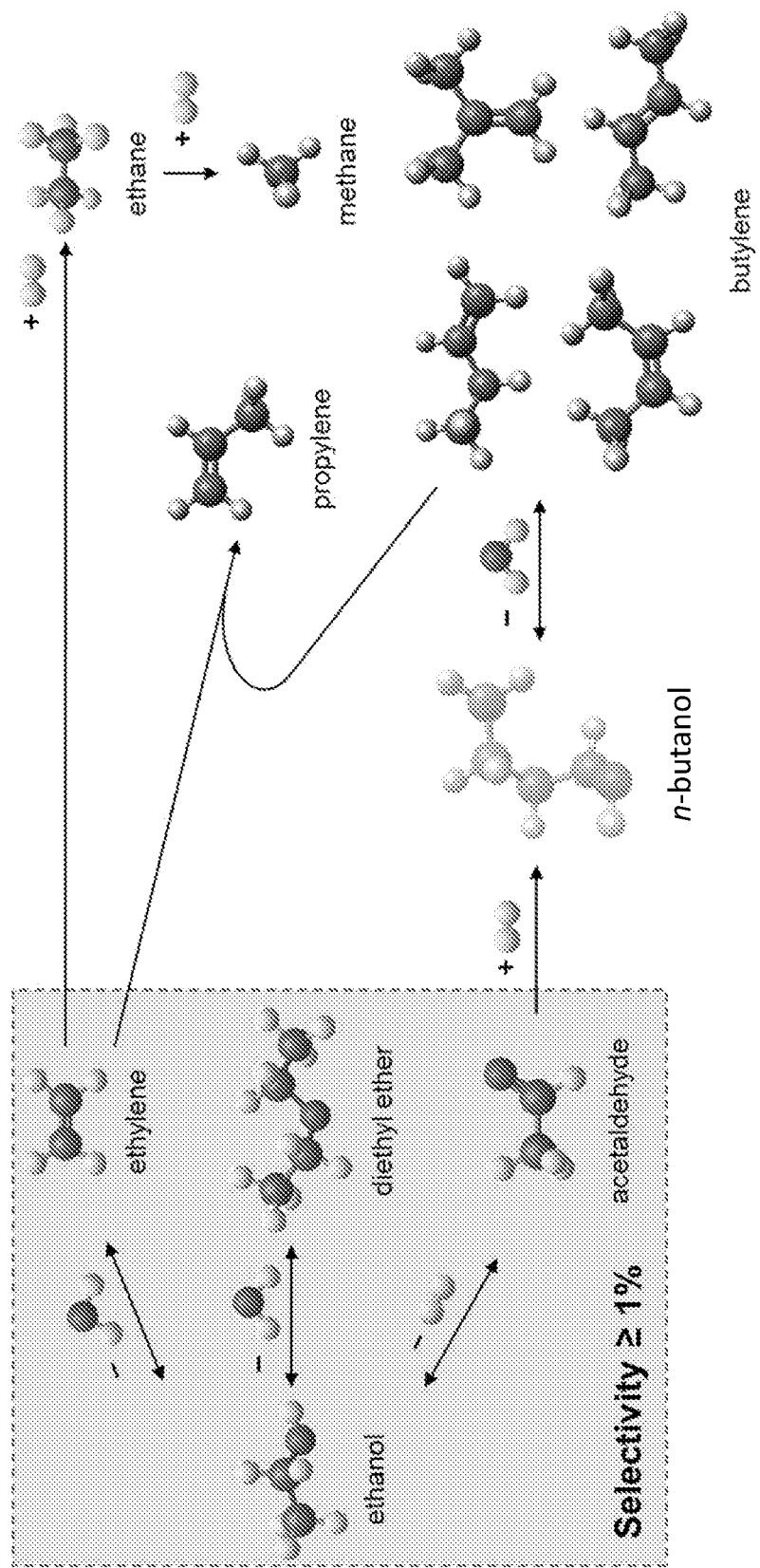
FIG. 4 shows a reaction scheme for ethanol conversion pathways on WZr-KIT-6 catalysts.

A variety of alcohols may be used in the present dehydration methods. Illustrative alcohols include ethanol, propanol (e.g., isopropanol), butanol (e.g., n-butanol), nonanol, glycerol and sugar alcohols such as sorbitol and xylitol. Other illustrative alcohols include 1,2-propanediol and 2,3-butanediol. The dehydration of alcohols provides one or more dehydration products, e.g., olefins, ethers, ketones, alkenols. In addition to dehydration reactions, other reactions such as dehydrogenation reactions, are also possible upon exposure of the original reactant alcohol to the bimetal-incorporated mesoporous silicate catalyst. Thus, aldehydes are possible products. Finally, intermediates may also undergo other reactions, e.g., hydrogenation, dehydration reactions, to form yet other products. FIG. 4 illustrates possible reaction schemes using ethanol as the original reactant alcohol to produce a variety of products including olefins, ethers, aldehydes, and alkanes. In the present dehydration methods, the alcohol may be provided in a feed, e.g., a gaseous feed also comprising a carrier gas (e.g., $N_2$). One or more alcohols may be used.

As noted above, the catalyst is a bimetal-incorporated mesoporous silicate. The term "bimetal" means that the catalyst includes at least two different metals, i.e., M and M', incorporated into the silicate. The term "metal-incorporated" and the like refer to the direct incorporation of the metal atoms into the silicate lattice structure such that the metal atoms replace silicon atoms. The term also means that the metal atoms are substantially completely incorporated into the silicate lattice structure. The term "substantially" means that all the metal atoms are incorporated into the silicate lattice structure or that all are incorporated with the exception of an amount too small to have any material effect on the catalytic performance of the catalyst. Evidence of metal-incorporation and the extent of incorporation may be derived from small-angle X-ray scattering (SAXS) pattern analysis (to assess modification of the unit-cell parameters of the silicate lattice structure), elemental analyses (to assess amount of metal incorporation) as well as ultraviolet-visible spectroscopy (to determine existence of metal-oxygen bonding and bond structure). The present metal-incorporated silicates are distinguished from materials made using grafting and impregnation approaches which create active species without direct incorporation of the metal atoms into the silicate lattice structure (or without substantial metal incorporation). The present catalysts are also distinguished from mixed metal oxide catalysts.

Various metals may be used, including transition metals. Illustrative metals include 4d transition metals such as Zr and Nb and 5d transition metals such as W. In embodiments, the bimetal-incorporated mesoporous silicate comprises W and a second transition metal.

The catalyst may be characterized by its lattice structure and symmetry (e.g., as determined from SAXS). In embodiments, the catalyst is characterized by a cubic structure with Ia3d symmetry (known as "KIT-6") or a cubic structure with Fm3m symmetry (known as "KIT-5"). Disordered bimetal-incorporated mesoporous silicates may also be used.

The catalyst may be further characterized by the mol % of each of the metals incorporated into the silicate lattice structure. The catalyst may be further characterized by various combinations of one or more of the following properties which may be determined using the techniques listed here and described in the Examples below: specific surface area (as determined from the Brunauer-Emmett-Teller (BET) equation), pore volumes and pore diameters (as determined from the Barrett-Joyner-Halenda (BJH) model), total acidity (as measured by ammonia temperature programmed desorption ($NH_3$-TPD)), and acid type, including the relative contents of Lewis and Brønsted acid sites (as determined using DRIFTS). The particular catalyst, its characteristics and properties may be selected depending upon the desired alcohol(s), to provide a desired conversion, and/or to provide a desired selectivity of a particular type(s) of products.

Illustrative bimetal-incorporated solid mesoporous silicate catalysts include $M_xM'_y$-KIT-6 and $M_xM'_y$-KIT-5, wherein M and M' are independently selected from Zr, Nb and W. In embodiments, the bimetal-incorporated solid mesoporous silicate catalyst is $W_xZr_y$-KIT-6 or $W_xZr_y$-KIT-5. The variables x and y refer to the mol % of each metal. The values of x and y are non-zero, but otherwise may vary. In embodiments, x and y are maximized so as to maximize the metal loading in the catalysts but without substantially disrupting the mesoporous structure of the catalysts. In embodiments, x and y are each in the range of greater than zero to about 10. As demonstrated in the Examples, below, the inventors were able to synthesize $W_{10}Zr_{10}$-KIT-6 without substantial disruption of the mesoporous structure of the catalyst. Illustrative catalyst species, along with their properties, are provided in Table 1 (see Example below). As Table 1 shows, illustrative specific surface areas include those in the range of from about 400 to about 1000 $m^2/g$; illustrative pore volumes include those in the range of from about 0.5 to about 1.5 $cm^3/g$; illustrative pore diameters include those in the range of from about 7 nm to about 10 nm; illustrative total acid amounts include those in the range of from about 0.1 to about 0.8 mmol $NH_3/g$; and illustrative Lewis/Brønsted acid ratios include those in the range of from about 0.5 to about 4. Regarding pore diameters, these pore diameters distinguish the present mesoporous catalysts from microporous catalysts (e.g., zeolites), the latter which have smaller pore sizes.

The present dehydration methods may be carried out using a variety of reactor systems. A suitable reactor system is a fixed bed reactor system (schematic not shown). The fixed bed reactor system delivers a carrier gas (e.g., $N_2$) at a selected mass flow rate and the desired alcohol reactant(s) at a selected partial pressure to the reactor containing a certain weight of catalyst to provide a selected weight hourly space velocity (WHSV), defined as the alcohol flow rate (g $h^{-1}$) per gram of catalyst (g) The reactor is configured to be maintained at a selected reaction temperature and selected reaction pressure. After processing, the mixture can then be collected and analyzed for product identification and yield. Various configurations of the fixed bed reactor system may be used. Other reactor systems may be used, e.g., continuous flow reactor systems in which a feed is handled via a continuous, flowing stream.

By "conditions," as that term is used with respect to the present dehydration methods, can refer to the parameters described above (i.e., mass flow rate of carrier gas, partial pressure of alcohol reactant(s), WHSV, reaction temperature, reaction pressure) as well as the reaction time. These conditions may be adjusted to achieve a desired conversion and/or selectivity. Illustrative reaction temperatures include those in the range of from about 300° C. to about 400° C. The reaction pressure may be ambient pressure. Illustrative partial pressures of alcohol reactants(s) include those in the range of from about 1 kPa to about 10 kPa or from about 3 kPa to about 9 kPa. The WHSV may be selected to achieve a maximum yield of a desired product, e.g., from about 1 to about 2 $h^{-1}$ to achieve a yield of about 99% ethylene. Illustrative reaction times for a fixed weight of catalyst include those of at least 0.5 hours, at least 1 hour, at least 1.5 hours, at least 2 hours, or in the range of from about 0.5 hours to 24 hours. Illustrative WHSV values include those of at least 0.5 $h^{-1}$, at least 1 $h^{-1}$, at least 2 $h^{-1}$ or in the range of from about 0.5 $h^{-1}$ to 100 $h^{-1}$.

As further described in the Example below, at least in some embodiments, the present dehydration methods are able to achieve high amounts of alcohol conversion. In embodiments, the present dehydration methods are able achieve an alcohol conversion of at least 50%, at least 60%, at least 70%, at least 75%, at least 80%, at least 85% or at least 90%. Alcohol conversion may be defined as [1-(moles of alcohol in reactor effluent/moles of alcohol in reactor feed)]*100. (See, e.g., "X" in Table 4 of the Example, below.) These alcohol conversion values may refer to the fresh catalyst, i.e., a catalyst which has not yet been exposed to an alcohol or regenerated as further described below.

As further described in the Examples below, at least in some embodiments, the present dehydration methods are able to achieve high selectivities, e.g., of a particular dehydration product. By way of illustration, for ethanol as the alcohol reactant, in embodiments, the present dehydration methods achieve a selectivity of ethylene of at least 50%, at least 60%, at least 70%, at least 75%, at least 80%, at least 85%. Product selectivity may be defined as moles of product in reactor effluent/moles of converted alcohol*100. (See, e.g., "$C_2H_4$" in Table 4 of the Example, below.)

Figure 6A:
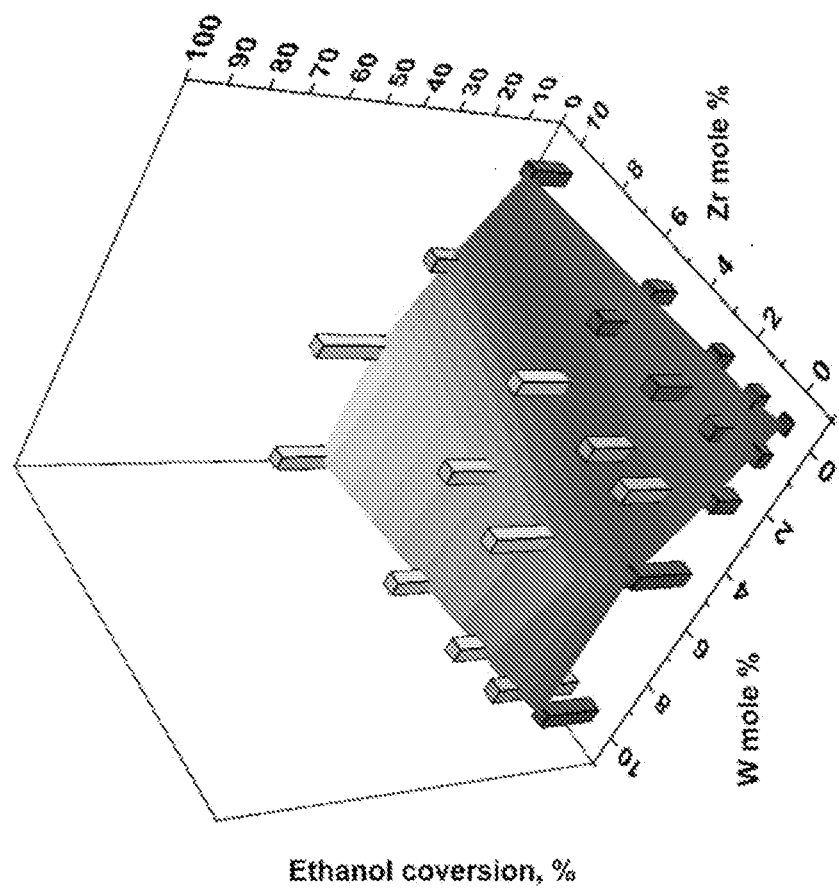
FIGS. 6A-6B show a comparison of experimental ethanol conversions on $W_xZr_y$-KIT-6 and sum of corresponding values on monometallic materials ($W_x$-KIT-6 and $Zr_y$-KIT-6) for TOS around 1 h (FIG. 6A) and TOS around 24 h (FIG. 6B). Operating conditions are listed in Table 4.
Figure 6B:
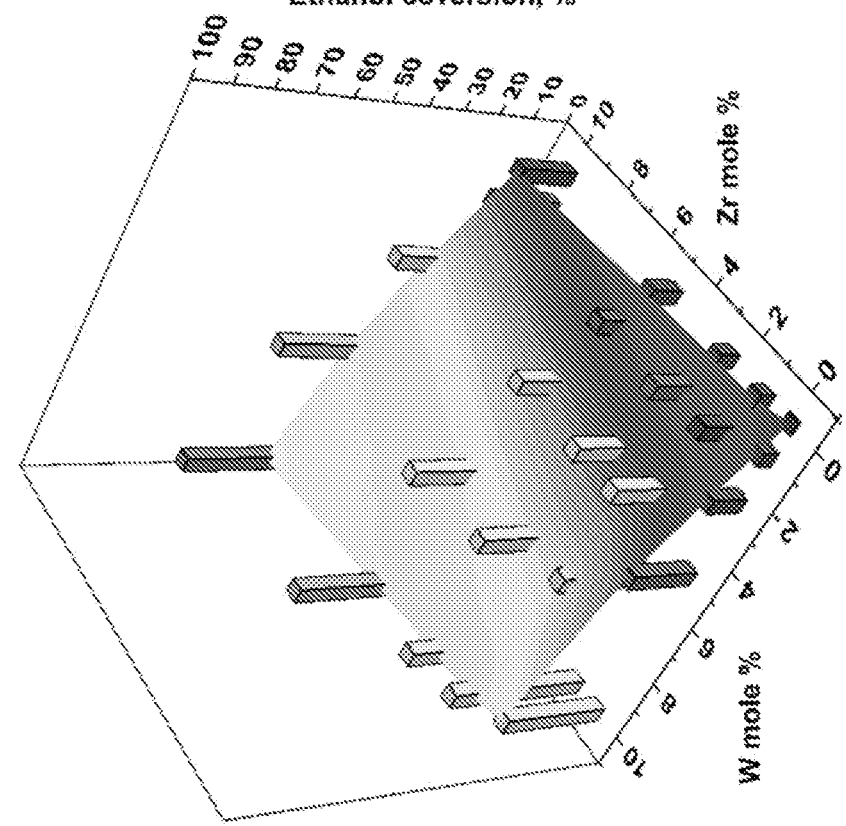

The inventors have found that the present bimetal-incorporated mesoporous silicate catalysts exhibit synergy in alcohol conversion as compared to their monometal counterpart catalysts. This is demonstrated in FIG. 6 which shows that the alcohol conversion of nearly all of the tested bimetal-incorporated mesoporous silicate catalysts is greater than the sum of the values from the respective monometal counterpart catalysts at the same loading. By way of illustration, the monometal counterpart catalysts for $W_{10}Zr_{10}$-KIT-6 are $W_{10}$-KIT-6 and $Zr_{10}$-KIT-6. The ethanol conversion value of $W_{10}Zr_{10}$-KIT-6 is 66.2% as compared to 28.0% for $W_{10}$-KIT-6 and 15.7% for $Zr_{10}$-KIT-6 (total of 43.7%).

The conversion/selectivities described above may refer to a particular set of reaction conditions, e.g., reaction temperature of 330° C., ambient pressure, alcohol WHSV of 9.47 $h^{-1}$, and reaction time of 0.75-1.5 hours or of 23-24 hours.

After use in the present dehydration methods, the bimetal-incorporated solid mesoporous silicate catalysts may be subjected to a regeneration step. In general, bimetal-incorporated solid mesoporous silicate catalysts which are contaminated with coke on their surfaces may be subjected to such a regeneration step. The regeneration step may comprise exposing the catalyst to air at a selected flow rate and an elevated temperature for a period of time. By "elevated" it is meant greater than room temperature. The flow rate, elevated temperature, and period of time may be selected to maximize the initial alcohol conversion value for the regenerated catalyst. By "initial alcohol conversion value" it is meant the alcohol conversion value determined at an initial time point (e.g., see the first square data points in FIGS. 5A-5D) at a particular set of reaction conditions (see the set of reaction conditions above). Illustrative flow rates include those in the range of from about 0.5 to about 2.0 L/(min-g catalyst); illustrative elevated temperatures include those in the range of from about 400° C. to about 550° C.; and illustrative periods of time include those in the range of from about 5 to about 24 h. The inventors have found that such regeneration steps are capable of actually increasing the activity of the regenerated catalyst as compared to the fresh catalyst. This is demonstrated by comparing FIG. 5C (fresh $W_{10}Zr_{10}$-KIT-6 exhibiting an initial ethanol conversion value of about 66%) to FIG. 5D (regenerated $W_{10}Zr_{10}$-KIT-6 exhibiting an initial ethanol conversion value of about 100%).

Figure 10:
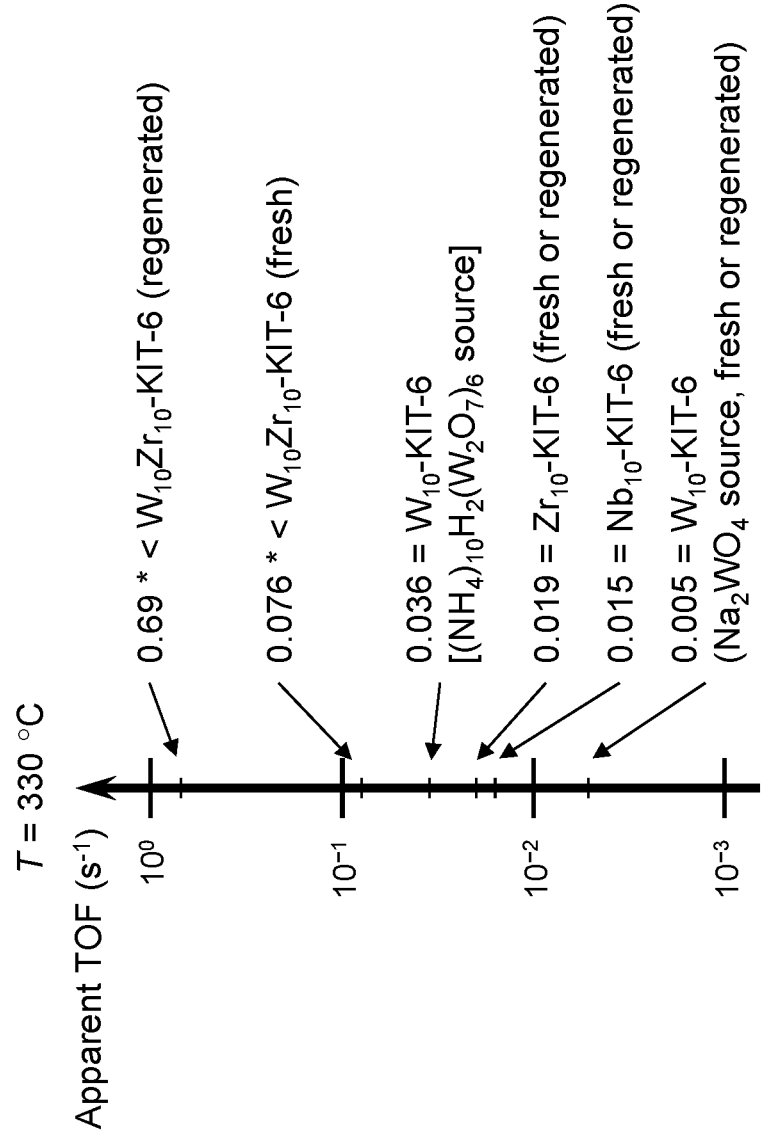
FIG. 10 shows the ethanol dehydration activity of bimetal-incorporated mesoporous silicate catalysts according to illustrative embodiments in comparison to monometal counterparts.

FIG. 10 shows the activity in terms of apparent turn-over frequency (TOF) of ethanol for embodiments of the present bimetal-incorporated mesoporous silicate catalysts ($W_{10}Zr_{10}$-KIT-6) and compares the activity to their monometal counterparts ($W_{10}$-KIT-6, $Zr_{10}$-KIT-6) and to another monometal catalyst, $Nb_{10}$-KIT-6 tested under similar conditions. The data for the present bimetal-incorporated mesoporous silicate catalysts and their monometal counterparts is derived from the experimental results presented in the Example, below. Regenerated catalysts were subjected to the regeneration step described above; fresh catalysts were not. Surprisingly, the regenerated $W_{10}Zr_{10}$-KIT-6 is at least 9 times more active than the fresh $W_{10}Zr_{10}$-KIT-6 and 13 times more active than the sum of its monometal counterparts; 19 times more than $W_{10}$-KIT-6, and 36 times more than $Zr_{10}$-KIT-6. These results are particularly surprising in view of the fact that the activity of the monometal catalysts is the same in the fresh and regenerated states.

Without wishing to be bound to any theory, the inventors believe that the surprising activity is related to the generation of new Brønsted and Lewis acid sites in the present bimetal-incorporated mesoporous silicate catalysts, as well as the strength of those acid sites. The structure and strength of these new Brønsted and Lewis acid sites are discussed in detail in the Example below. The Example also demonstrates that the x and y amounts may be tuned to achieve these new acid sites. Regarding the new Brønsted acid sites, in embodiments, the bimetal-incorporated mesoporous silicate catalyst comprises Brønsted acid sites corresponding to protons of hydroxyl groups bound to M, M', or both, of a M-O-M' species, or a cluster of M-O-M' species, in the catalyst. In embodiments, the catalyst comprises Brønsted acid sites exhibiting a proton shift in a range of from 2 to 12 ppm in $^1H$ magic angle spinning (MAS) NMR. This includes proton shifts of at least 4.7 ppm or of 4.7 ppm. Regarding the new Lewis acid sites, in embodiments, the catalyst further comprises Lewis acid sites corresponding to M, M', or both, of the M-O-M' species, or the cluster of M-O-M' species, in the catalyst. In embodiments, the catalyst further comprises Lewis acid sites exhibiting a pyridinium signal of in a range of from 220 to 280 ppm in $^{15}N$ cross-polarization (CP) MAS NMR. This includes pyridinium signals of no more than 261 ppm or of 261 ppm.

It is further believed that the surprising activity of the regenerated bimetal-incorporated mesoporous silicate catalyst is related to the emergence of additional, stronger Brønsted acid sites. In embodiments, the bimetal-incorporated mesoporous silicate catalyst comprises Brønsted acid sites corresponding to protons bound to oxygen in a heteropolymeric network of M, M', and O in the catalyst. In embodiments, one of the metals of the catalyst is W and the heteropolymeric network is a heteropolytungstate network. In embodiments, the catalyst comprises Brønsted acid sites exhibiting a proton shift in a range of from 3 to 12 ppm in $^1$H MAS NMR. This includes proton shifts of at least 5.8 ppm or of 5.8 ppm.

Methods for making the bimetal-incorporated mesoporous silicate catalysts are also provided. In an embodiment, a method for making a bimetal-incorporated mesoporous silicate catalyst comprises mixing a silicate precursor, a first metal precursor and a second metal precursor with a structure directing composition comprising a structure directing agent and a co-solvent at a temperature and for a period of time; and subjecting the mixture to a hydrothermal treatment to form the bimetal-incorporated solid mesoporous silicate catalyst. The silicate precursor provides a source of silica, the first metal precursor provides a source of the first metal (M), and the second metal precursor provides a source of the second metal (M'). The structure directing agent and the co-solvent facilitate formation of the silicate lattice structure. Illustrative compounds, temperatures and times are provided in the Example, below. The term "hydrothermal treatment" refers to crystal formation (from the silica and metal precursors) using aqueous solutions at high temperature and under high pressure. Illustrative conditions for the hydrothermal treatment are provided in the Example, below.

In addition, bimetal-incorporated mesoporous silicate catalysts having high activity may be made from coke-contaminated bimetal-incorporated mesoporous silicate catalysts by exposure to air at an elevated temperature and for a period of time as described above. Such bimetal-incorporated mesoporous silicate catalysts will comprise Brønsted acid sites having a strength greater than those of the coke-contaminated catalyst.

The bimetal-incorporated mesoporous silicate catalysts themselves are also provided. Thus, the catalysts may be used in a variety of reactions in addition to the alcohol dehydration reactions described above.

Example

Abstract

Using a one-pot synthesis technique, tungsten and zirconium were simultaneously incorporated into ordered mesoporous KIT-6 framework. A series of such materials, denoted as WZr-KIT-6, were synthesized with W and Zr loadings ranging from 0 mol % to 10 mol % each. At sufficiently high Zr loadings, ssNMR spectra of neat as well as pyridine-adsorbed catalyst confirm that the fresh WZr-KIT-6 materials exhibit both Lewis and Brønsted acid sites of high strength, resulting in correspondingly high ethylene yields during ethanol dehydration. Such yields surpass those observed on $W_x$-KIT-6 and $Zr_y$-KIT-6 materials with identical W and Zr loadings as in $W_xZr_y$-KIT-6. Unexpectedly, air regeneration of the spent WZr-KIT-6 catalyst further enhances ethanol dehydration activity, with initial ethylene yields approaching those reported with HZSM-5 and SAPO-34 catalysts at similar operating conditions. This enhancement correlates with ssNMR evidence of the formation of additional strong Brønsted acid sites following the regeneration step, which, without wishing to be bound to any theory, is thought to be from the water produced during combustion of the coke deposits. On the basis of ssNMR characterization of acid strength, these acidic protons are assigned to the hydroxyl groups bound to metals in W—O—Zr structures and to the stronger acidic protons on heteropolytungstate structures. The formation of strong Brønsted acid sites, comparable to those observed in H-ZSM-5 and H-Beta, in mesoporous WZr-KIT-6 materials are particularly attractive for reactions that are prone to rapid deactivation by coking in microporous catalysts.

Materials

Catalysts with varying W and Zr loadings in the KIT-6 framework were prepared using a one-pot method. Tetraethoxysilane was purchased from Acros Organics. Ammonium metatungstate and $ZrOCl_2$ were purchased from Alfa Aesar. Pluronic P123 triblock copolymer was purchased from Sigma-Aldrich. Concentrated hydrochloric acid (37 wt. %) and 1-butanol were purchased from Fisher. Silica particles, used as diluent in the catalyst bed, were purchased from Sigma-Aldrich and sieved to match the particle sizes of catalyst pellets (250-425 μm). The HZSM-5 (Si/Al=15 mol/mol) for benchmarking was obtained from Nexceris (batch identical to that in Nash, C. P. et al., Applied Catalysis A: General 2016, 510, 110-124). Zeolite Beta (Si/Al=30 mol/mol) was purchased from Zeolyst.

Ethanol (99.5%, anhydrous) used in the dehydration studies was purchased from Sigma-Aldrich. For the diffuse-reflection Fourier-transformed infrared (DRIFT) characterization of catalysts, pyridine (≥99%) was purchased from Fisher. For solid-state NMR sample preparation, deuterated pyridine-$d_5$ (99.5 atom % D) was purchased from Alfa Aesar. Pyridine-$^{15}$N (≥98 atom % $^{15}$N) was purchased from Cambridge Isotope. Zero-grade air was supplied on site from a Matheson Zero Air Generator. Argon (Ultra High Purity, 99.999%) was purchased from Matheson. Nitrogen (High Purity, 99.99%) and helium (High Purity, 99.995%) were purchased from Matheson. Ethylene standard (5.0% ethylene in nitrogen, 19.9 ppm ethane) was purchased from Matheson. Acetone (≥99.5%) was purchased from Fisher. 1-Butanol (anhydrous, 99.9%, packed under Argon, ChemSeal™) was purchased from Alfa Aesar. The helium and argon gases were purified by passing through Alltech Oxo-Trap, Alltech Hydrocarbon Trap and Alltech Hydropurge II to remove oxygen, hydrocarbons and moisture, respectively. Acetone was desiccated with anhydrous sodium sulfate. Other materials were used as received without further purification.

Experiments

Catalyst Preparation

The catalysts were prepared using a one-pot synthetic technique and the co-addition of W and Zr sources. The catalysts were labelled as $W_xZr_y$-KIT-6, where x and y represent the mole percentages of the W and Zr sources in the synthesis gel, respectively. The sample without any metal incorporation was labelled as Si-KIT-6. In general, the WZr-KIT-6 catalysts were prepared by dissolving 3.7 g Pluronic® P123 in 130 g deionized water and 6.8 g hydrochloric acid solution (37 wt %) at 35° C. Then 3.7 g n-butanol was added and after stirring for 1 h, 8 g of tetraethoxysilane (TEOS), appropriate amounts of zirconyl chloride, and ammonium metatungstate were added and the stirring continued for at least 15 h. Finally, the synthesis mixture was heated for 24 h at 100° C. and the resulting solid product was filtered, dried at 100° C. and calcined in air at 550° C. for 5 h.

Physiochemical Characterization

The textural properties of the materials were measured via nitrogen sorption in liquid nitrogen (77 K) on a Quantachrome Autosorb iQ instrument following evacuation at 300° C. for 5 h. The Brunauer-Emmett-Teller (BET) equation was used to estimate specific surface area. The Barrett-Joyner-Halenda (BJH) model was used to estimate pore volumes and pore diameter distributions.

The total acidity of the WZr-KIT-6 samples was measured by ammonia temperature programmed desorption ($NH_3$-TPD) with a Micromeritics AutoChem 2910 instrument. The samples were treated in flowing He at 550° C. prior to $NH_3$ treatment, and the desorption was recorded with a thermal conductivity detector (TCD) in the 100-550° C. range. The relative contents of Lewis and Brønsted acid sites on the fresh and used WZr-KIT-6 materials were estimated from DRIFTS on a Bruker Tensor 27 instrument following pyridine adsorption at ambient conditions. Prior to analysis, approximately 100 mg catalyst samples were loaded into the 20 ml sample vials, followed by addition of 0.15 ml pyridine. The samples were stored at room temperature for 24 h, then placed in a vacuum oven heated to 90° C. for 12 h, purged three times by alternating vacuum (−29.6 inHg gauge=−749 mmHg) and argon flow, and stored in vacuum for 12 h.

Solid-state NMR (ssNMR) experiments were conducted for Si-KIT-6, $W_{10}$-KIT-6, $Zr_{10}$-KIT-6, and $W_{10}Zr_{10}$-KIT-6 samples. Generally, the samples (about 0.3 g) were pretreated in a stainless steel tube at 550° C. and ambient pressure in flowing zero-grade air (150 sccm) for 24 h to ensure removal of any adsorbents, then purged with argon flow (150 sccm for 30 min) prior to transferring the sealed tube to a glovebox. 4 mm $ZrO_2$ rotors were loaded with the samples under a dry argon environment in the glovebox. Samples adsorbed with pyridine-$d_5$ or pyridine-$^{15}N$ were maintained at 50° C. for 24 h to equilibrate. The ssNMR experiments were performed on a 400 MHz Bruker instrument with magic angle spinning (MAS) at 10 kHz. Cross polarization (CP) was used for $^{15}N$ spectra. Tetramethylsilane (TMS, liquid, set to 0 ppm) and $^{15}N$-glycine (powder, set to 33.4 ppm) were used as external standards for measuring $^1H$ and $^{15}N$ chemical shifts, respectively. Spectra were collected for fresh catalysts and those adsorbed with isotope-labelled pyridine.

Ethanol Conversion

The ethanol conversion and product selectivity on the WZr-KIT-6 catalysts were measured in a fixed-bed reactor. An ISCO syringe pump was used for more stable inlet flow of the ethanol feed. Also, the effluent gas stream from the fixed-bed reactor was split to pass about 20 mL/min through the sample loop in the Hewlett-Packard 5890 II GC in order to ensure constant operating pressure in the reactor. The GC was equipped with an Agilent J&W HP-PLOT/Q megabore column (30 m×0.53 mm×40.00 µm) and a flame-ionization detector (FID). To evaluate the performance of the fresh and regenerated WZr-KIT-6 catalysts, fixed-bed reactor experiments were performed with catalyst particle sizes in the 250-425 µm range, ethanol partial pressure of 3 kPa in nitrogen, and weight hourly space velocity (WHSV) of 9.47 $h^{-1}$. The reaction temperature was maintained at 330° C., unless otherwise specified. Prior to reaction, fresh catalysts were pretreated in flowing zero-grade air (150 sccm), with a ramping rate of 2° C./min to 550° C., and then maintained for 8 h. Catalyst regeneration was performed in the reactor following a run with either flowing zero-grade air (150 sccm) or nitrogen at 550° C. for 8 h.

To investigate the reaction pathway for butylene formation, 5 mol % ethylene in $N_2$ was fed to either fresh or used (following an 8 h run with ethanol) $W_3Zr_{2.5}$-KIT-6 and $W_{10}Zr_{10}$-KIT-6 catalysts, representing formulations that show synergy. This experiment was followed by another run in which a feed stream containing 5 mol % ethylene and 0.5 mol % ethanol in nitrogen was used with the fresh $W_3Zr_{2.5}$-KIT-6 catalyst.

To probe the presence of relatively strong Brønsted acid sites on a $W_3Zr_{2.5}$-KIT-6 catalyst (representative catalyst exhibiting good reproducibility), experiments were also performed sequentially at 300, 330 and 360° C., using either neat ethanol feed or an ethanol feed containing 3.8 mol % acetone (a weak base that may interact with moderate or strong Brønsted sites) with the $W_3Zr_{2.5}$-KIT-6 samples. For experiments with each feed, a fresh catalyst sample was pretreated under reaction conditions for 12 h when stable conversion and selectivities were observed.

In order to determine the amount of species formed on the spent catalyst sample, thermogravimetric analysis was performed on $W_{10}Zr_{10}$-KIT-6 catalyst samples. TGA was performed on the fresh sample, a spent sample with a total run time of 24 h, and a regenerated sample were heated to 900° C. in flowing air (100 sccm) at a ramp rate of 10° C./min. A spent sample was also analyzed sequentially by TGA, first in flowing $N_2$ (100 sccm) and then in flowing air (100 sccm).

Results and Discussion

Characterization of Fresh Catalysts

Figure 1:
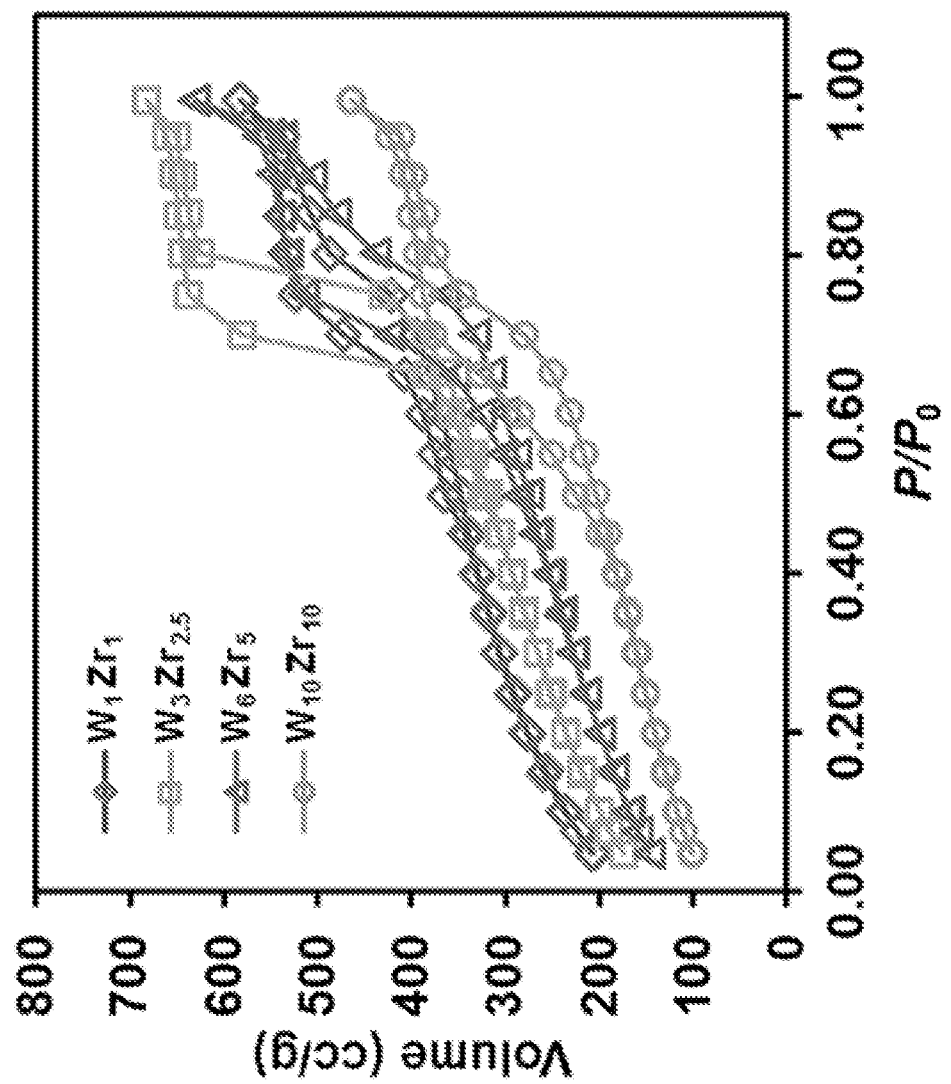
FIG. 1 shows typical $N_2$ sorption isotherms for WZr-KIT-6 catalysts according to illustrative embodiments.

The fresh $W_xZr_y$-KIT-6 materials with various W and Zr loadings showed a typical type IV nitrogen sorption isotherm. (FIG. 1.) As summarized in Table 1, the specific surface area of both the monometallic formulations and the bimetallic formulations generally decreased at higher metal loadings, from 980 corresponding to monometallic Zr loading of 1 mol % to 438 $m^2$/g corresponding to a metal loading of 10 mol % W and 5 mol % Zr. The average mesopore sizes range from 8.5-9.6 nm at the lower metal loadings, and decreases sharply at high metal loadings (to 7.1 nm on $W_{10}Zr_{10}$-KIT-6). The pore size distribution (data not shown) reveals that the majority of the pores are in the mesoporous range (6.5-9.5 nm). The clear trends in the population of pores in the 2.7-4.3 nm range indicate that excess tungsten causes deformation of the mesoporous structure, while the addition of zirconium mitigates the effect. The excess tungsten possibly induces structural deformation by forming distorted isopolytungstate or heteropolytungstate wherein the tungsten exhibits versatile coordination numbers (4-9) with oxygen ligands. On all WxZry-KIT-6 materials, the $NH_3$-TPD profiles in the 100-550° C. range clearly show two major desorption peaks in the 165-179 and 210-246° C. ranges. (Data not shown.) The amounts of both types of acid sites increase with either W or Zr loading (data not shown). On the HZSM-5 sample (Si/Al=15 mol/mol), whose performance for ethanol conversion is compared experimentally with WZr-KIT-6 materials, two major desorption peaks are observed around 270 and 470° C. Zeolite Beta is known to exhibit weaker acidity in comparison to HZSM-5, with three major $NH_3$ desorption peaks around 105, 200, and 390° C. These comparative observations confirm the existence of acid sites on WxZry-KIT-6 catalysts that are weaker than those on HZSM-5 and the strongest type (390° C.) on Beta Zeolite but stronger than the two weak types of acid sites (105 and 200° C.) on Beta Zeolite. The $NH_3$-TPD profile beyond 550° C. may not be reliably interpreted, given that the maximum calcination temperature during WZr-KIT-6 synthesis was 550° C.

TABLE 1

Textural and acidity properties of WZr-KIT-6 catalysts with various metal loadings.

| # | $W_xZr_y$,[a] | $S_{BET}$,[b] $m^2/g$ | $V_{P, BJH}$,[c] $cm^3/g$ | $D_{P, BJH}$,[d] nm | Total acid amount,[e] mmol $NH_3$/g | Lewis/Brønsted acid ratio[f] |
|---|---|---|---|---|---|---|
| 1 | $W_0Zr_0$ | 863 | 1.30 | 8.5 | 0.04 | — |
| 2 | $W_0Zr_1$ | 980 | 1.65 | 9.3 | 0.19 | L |
| 3 | $W_0Zr_{2.5}$ | 881 | 1.42 | 9.3 | 0.40 | L |
| 4 | $W_0Zr_5$ | 810 | 1.07 | 9.3 | 0.49 | L |
| 5 | $W_0Zr_{10}$ | 656 | 0.91 | 7.1 | 0.47 | 2.24 |
| 6 | $W_1Zr_0$ | 927 | 1.44 | 6.4 | 0.26 | 6.49 |
| 7 | $W_1Zr_1$ | 953 | 0.90 | 9.6 | 0.19 | 2.30 |
| 8 | $W_1Zr_{2.5}$ | 782 | 1.02 | 8.2 | 0.37 | 2.29 |
| 9 | $W_1Zr_5$ | 742 | 1.29 | 7.3 | 0.46 | 3.33 |
| 10 | $W_1Zr_{10}$ | 730 | 1.11 | 8.1 | 0.68 | 1.93 |
| 11 | $W_{2.5}Zr_0$ | 599 | 0.64 | 9.6 | 0.18 | 3.07 |
| 12 | $W_3Zr_1$ | 747 | 1.05 | 9.6 | 0.27 | 3.87 |
| 13 | $W_3Zr_{2.5}$ | 828 | 1.06 | 9.6 | 0.29 | 1.19 |
| 14 | $W_3Zr_5$ | 687 | 1.04 | 9.6 | 0.45 | 1.90 |
| 15 | $W_3Zr_{10}$ | 663 | 0.98 | 8.0 | 0.65 | 1.96 |
| 16 | $W_5Zr_0$ | 584 | 0.83 | 9.6 | 0.28 | 0.99 |
| 17 | $W_6Zr_1$ | 613 | 0.69 | 9.6 | 0.25 | 1.29 |
| 18 | $W_6Zr_{2.5}$ | 568 | 0.75 | 9.6 | 0.46 | 1.24 |
| 19 | $W_6Zr_5$ | 711 | 0.97 | 9.6 | 0.45 | 1.44 |
| 20 | $W_6Zr_{10}$ | 668 | 0.92 | 7.6 | 0.59 | 1.43 |
| 21 | $W_{10}Zr_0$ | 534 | 0.75 | 9.5 | 0.45 | 1.26 |
| 22 | $W_{10}Zr_1$ | 468 | 0.71 | 9.5 | 0.23 | 0.67 |
| 23 | $W_{10}Zr_{2.5}$ | 500 | 0.80 | 9.6 | 0.58 | 0.58 |
| 24 | $W_{10}Zr_5$ | 438 | 0.61 | 7.9 | 0.47 | 1.11 |
| 25 | $W_{10}Zr_{10}$ | 525 | 0.75 | 7.1 | 0.58 | 1.22 |

[a] subscripts - W and Zr mole %,
[b] specific surface area estimated by BET method,
[c] pore volume estimated by BJH model,
[d] pore diameter estimated by BJH model,
[e] total acidity determined by $NH_3$-TPD,
[f] Lewis to Brønsted acid ratio estimated by DRIFTS of pyridine-titrated samples, L for predominantly Lewis acid.

To discern the possible existence of acid sites stronger than those revealed by $NH_3$-TPD, $^1H$ and $^{15}N$ ssNMR techniques were used with an isotopically labeled strongly basic probe molecule, pyridine. The DRIFT spectra of pyridine adsorbed catalyst samples clearly indicate that the fresh WZr-KIT-6 materials with various W and Zr loadings possessed both Lewis and Brønsted acid sites. In contrast, Zr-KIT-6 materials with metal loadings <10 mol % possess mostly Lewis acid sites (Table 1, rows 2-4). As shown in Table 1, the total acidity ($a_{total}$) measured by $NH_3$-TPD and the relative ratios of Lewis/Brønsted acids ($R_{L/B}$) estimated from pyridine-DRIFTTS do not exhibit any obvious trend.

Table 2 gives estimated values of the Lewis and Brønsted acid sites from deconvolution of the pyridine-DRIFT spectra. The following empirical correlations combine the quantitative $NH_3$-TPD results (acidity, $a_{L+B}$, mmol/g) and the estimated Lewis to Brønsted acid ratio, $R_{L/B}$. In general, the Brønsted acidity increased with both W and Zr loading, while the Lewis acidity increased with Zr loading and decreased with W loading.

$$a_{Brønsted} = \frac{a_{total}}{1+R_{L/B}}, \quad a_{Lewis} = \frac{a_{total}R_{L/B}}{1+R_{L/B}}$$

TABLE 2

Estimated Lewis and Brønsted acid contents (mmol/g) of WZr-KIT-6

| $W_xZr_y$ | Acid site | $W_0$ | $W_1$ | $W_{2.5}$ | $W_5$ | $W_{10}$ |
|---|---|---|---|---|---|---|
| $Zr_0$ | L | — | 0.23 | 0.14 | 0.14 | 0.25 |
|  | B | — | 0.03 | 0.04 | 0.14 | 0.20 |
|  |  | $W_0$ | $W_1$ | $W_3$ | $W_6$ | $W_{10}$ |
| $Zr_1$ | L | 0.19 | 0.13 | 0.21 | 0.14 | 0.09 |
|  | B | — | 0.06 | 0.06 | 0.11 | 0.14 |
| $Zr_{2.5}$ | L | 0.40 | 0.26 | 0.16 | 0.25 | 0.21 |
|  | B | — | 0.11 | 0.13 | 0.21 | 0.37 |
| $Zr_5$ | L | 0.49 | 0.35 | 0.29 | 0.27 | 0.25 |
|  | B | — | 0.11 | 0.16 | 0.18 | 0.22 |
| $Zr_{10}$ | L | 0.32 | 0.45 | 0.43 | 0.35 | 0.32 |
|  | B | 0.15 | 0.22 | 0.22 | 0.24 | 0.26 |

The $^1H$ MAS spectra of fresh $W_{10}$-KIT-6, $Zr_{10}$-KIT-6, and $W_{10}Zr_{10}$-KIT-6 samples are shown in FIGS. 2A, 2C and 2E, respectively. The signal around 1.8 ppm is assigned to silanol groups. The signals at 3.7, 5.2 (FIG. 2C), and 4.7 (FIG. 2E) ppm are assigned to Brønsted acid sites. Compared to the $W_{10}$-KIT-6 catalyst, the fresh $W_{10}Zr_{10}$-KIT-6 catalyst shows a clear signal at 4.7 ppm attributed to Brønsted acid sites. Interestingly, HZSM-5 zeolite shows Brønsted acid sites at 4.0 ppm,[17] suggesting that the fresh $W_{10}Zr_{10}$-KIT-6 catalyst possesses Brønsted acid sites of higher strength. The major $^1H$ signals shifted to lower values (4.6-9.9 ppm) following pyridine-$d_5$ adsorption on the samples suggesting that the majority of the Brønsted acid sites on these materials are weak and perhaps similar to those on Nb-KIT-6. The narrow signals in the 6.8-7.4 ppm range belong to non-deuterated $^1$H atoms in pyridine.

Figures 3A, 3B, 3C, 3D:
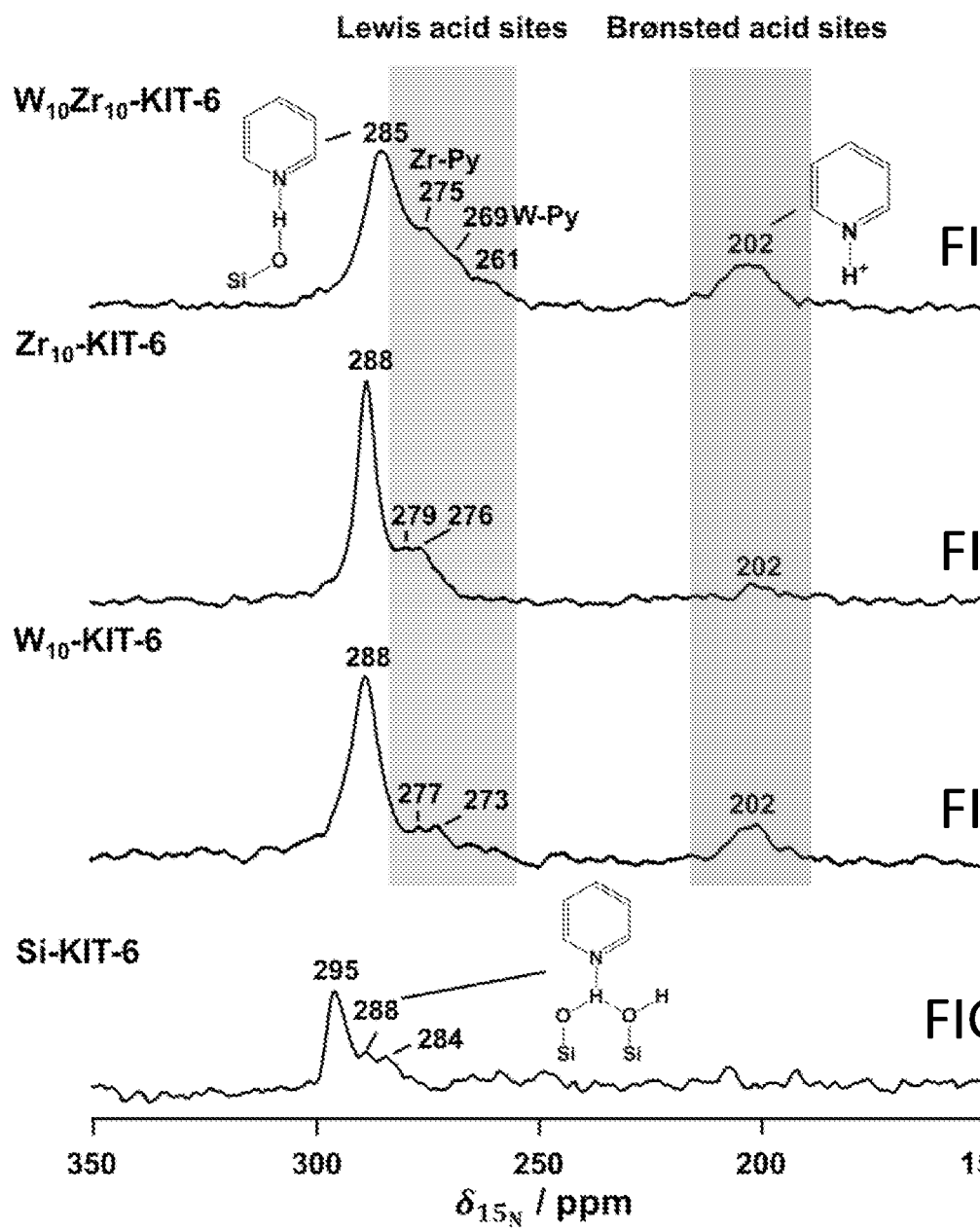
FIGS. 3A-3D show $^{15}N$ CP MAS spectra of fresh catalyst samples titrated with $^{15}N$-pyridine. Fresh $W_{10}Zr_{10}$-KIT-6 (FIG. 3A), fresh $Zr_{10}$-KIT-6 (FIG. 3B), fresh $W_{10}$-KIT-6 (FIG. 3C), fresh Si-KIT-6 (FIG. 3D).

In the $^{15}$N CP MAS spectra of fresh $W_{10}Zr_{10}$-KIT-6, $W_{10}$-KIT-6, $Zr_{10}$-KIT-6, and Si-KIT-6 materials titrated with $^{15}$N-pyridine (FIGS. 3A-3D), no physisorbed pyridine was observed around 314-318 ppm. In the Si-KIT-6 spectra (FIG. 3d), the signals at 295, 288 and 285 ppm are assigned to adsorbed pyridine on isolated silanol groups, vicinal silanol groups and silanol nests, respectively. Compared to Si-KIT-6, the signals for isolated silanol groups at 295 ppm are shifted to 288 ppm on $W_{10}$-KIT-6 (FIG. 3B) and $Zr_{10}$-KIT-6 (FIG. 3C), suggesting interaction of the silanol groups with Zr and W, respectively. The two signals at 279 and 276 ppm on $Zr_{10}$-KIT-6 are assigned to the adsorbed pyridine on Lewis acid sites with different coordination numbers to the Zr center. Similar signals at 277 and 273 ppm are seen on $W_{10}$-KIT-6. On $W_{10}Zr_{10}$-KIT-6 (FIG. 3A), the silanol signal is further shifted to 285 ppm, suggesting even stronger interaction of the silanol groups with the species on the catalyst. Further, incorporation of the metals induced Brønsted acid sites as evidenced by the pyridinium signals around 202 ppm. The $^{15}$N chemical shifts of pyridine bound to Lewis acid sites are thought to correlate with the metal electronegativity. The signals at 275 ppm and 269 ppm on $W_{10}Zr_{10}$-KIT-6 (FIG. 3A) are attributed to the adsorption complexes of pyridine with Zr and W, respectively. The signal around 261 ppm was not observed on either $W_{10}$-KIT-6 or $Zr_{10}$-KIT-6. Without wishing to be bound to any theory, this signal is thought to be partially responsible for the synergy exhibited by the fresh catalysts for ethanol dehydration. The new species may be generated due to the binding of hydrolyzed W and Zr sources during the one-pot synthesis which induces the formation of W—O—Zr structures. The metal centers of such structures may both interact with molecules exhibiting basicity (i.e. the substrate ethanol or the probe pyridine).

Ethanol Conversion Studies

During performance evaluation of the $W_xZr_y$-KIT-6 for ethanol conversion, major products (with selectivities ≥1%) detected by the FID include ethylene, ethane, acetaldehyde and diethyl ether (DEE), while minor products include methane, propylene, and the 4 butene isomers. Chromatograms from the online analysis of these products were obtained (data not shown.) Based on this product spectrum, a plausible reaction scheme is provided in FIG. 4. The corresponding reaction equilibrium constants at reaction condition (330° C., 1 atm) are summarized in Table 3.

base sites that are near each other favor DEE formation. The formation of acetaldehyde is attributed to dehydrogenation involving basic sites. Dihydrogen was indeed observed with a thermoconductivity detector (TCD). The methane is formed possibly due to hydrocracking of higher hydrocarbons. Propylene could form via metathesis of ethylene and butene; however, this reaction is significantly inhibited by oxygenates, including water and ethanol. In similar reaction systems, $C_4$ compounds have been reported to form on strong acid sites by ethylene dimerization, and/or from n-butanol via condensation of acetaldehyde in the presence of hydrogen. However, when feeding 5.0 mol % ethylene in nitrogen to the $W_3Zr_{2.5}$-KIT-6 and $W_{10}Zr_{10}$-KIT-6 catalysts, no significant $C_4$ formation was observed on either the fresh catalyst or the catalyst treated with ethanol at 330° C. In contrast, when co-feeding 5 mol % ethylene and 0.5 mol % ethanol in nitrogen to $W_3Zr_{2.5}$-KIT-6, the C balance based on the ethylene formed and other products closed within ~98% of the ethanol converted. The formation of butylene isomers was thus attributed to sequential acetaldehyde condensation and butanol dehydration. Because n-butanol dehydration is favored thermodynamically (Table 3) at high kinetic rates, its observed selectivity in the reactor effluent was <1% on all WZr-KIT-6 materials. Indeed, when n-butanol alone was used as feed, it was totally converted on $W_3Zr_{2.5}$-KIT-6 at otherwise identical operating conditions (T=330° C., $P_{BuOH}$=1.6 kPa, and WHSV=4.71 h$^{-1}$) with product selectivities as follows: 0.2% $C_2H_4$, 9.8% $C_3H_6$, 28.4% n-$C_4H_8$, 0.2% i-$C_4H_8$, 30.7% trans-2-$C_4H_8$, and 30.1% cis-2-$C_4H_8$. The kinetic $C_4H_8$ isomer selectivities differed significantly from the predicted equilibrium distribution (Table 3). The significant formation of cis-2-$C_4H_8$ suggests that n-butanol dehydration occurs possibly via an $E_1$ mechanism where relatively strong Brønsted sites are required to form carbocations rather than via the $E_2$ mechanism which is subject to significant steric hindrance. The presence of Brønsted acid sites in the $W_xZr_y$KIT-6 catalysts and its mesoporous nature render the $E_2$ mechanism less likely.

Temporal ethanol conversion profiles of WZr-KIT-6 materials with various W and Zr loadings showed a deactivating trend between 4-18 h on stream (FIGS. 5A-5D). The ethanol conversion as well as the line-out period (when the conversion profiles reach an apparent steady state) increase

TABLE 3

Equilibrium constants of reactions on WZr-KIT-6 catalysts

| | Reaction | Equilibrium Constant[a] |
|---|---|---|
| Major | $CH_3CH_2OH \rightleftharpoons CH_2=CH_2 + H_2O$ | $5.85 \times 10^4$ kPa |
| | $2CH_3CH_2OH \rightleftharpoons (CH_3CH_2)_2O + H_2O$ | 4.49 |
| | $CH_3CH_2OH \rightleftharpoons CH_3CHO + H_2$ | 356 kPa |
| | $CH_2=CH_2 + H_2 \rightleftharpoons CH_3CH_3$ | $2.10 \times 10^3$ kPa$^{-1}$ |
| Minor | $CH_3CH_3 + H_2 \rightleftharpoons 2CH_4$ | $1.55 \times 10^6$ |
| | $2CH_3CHO + 2H_2 \rightleftharpoons CH_3(CH_2)_3OH + H_2O$ | 0.0294 kPa$^{-2}$ |
| | $CH_3(CH_2)_3OH \rightleftharpoons$ n-$C_4H_8 + H_2O$ | $1.89 \times 10^6$ kPa |
| | $CH_3(CH_2)_3OH \rightleftharpoons$ cis-2-$C_4H_8 + H_2O$ | $3.05 \times 10^6$ kPa |
| | $CH_3(CH_2)_3OH \rightleftharpoons$ trans-2-$C_4H_8 + H_2O$ | $4.05 \times 10^6$ kPa |
| | $CH_3(CH_2)_3OH \rightleftharpoons$ i-$C_4H_8 + H_2O$ | $9.45 \times 10^6$ kPa |
| | $CH_2=CH_2 +$ trans-2-$C_4H_8 \rightleftharpoons 2CH_2CH=CH_2$ | 10.3 |
| | $CH_2CH=CH_2 + H_2O \rightleftharpoons CH_3CH_2CH_2OH$ | $8.66 \times 10^{-7}$ kPa$^{-1}$ |

[a]Equilibrium constants of gas phase reactions at 330° C. and 1 atm estimated with Aspen Plus 8.6 with Peng-Robinson EoS.

Figures 5A, 5B:
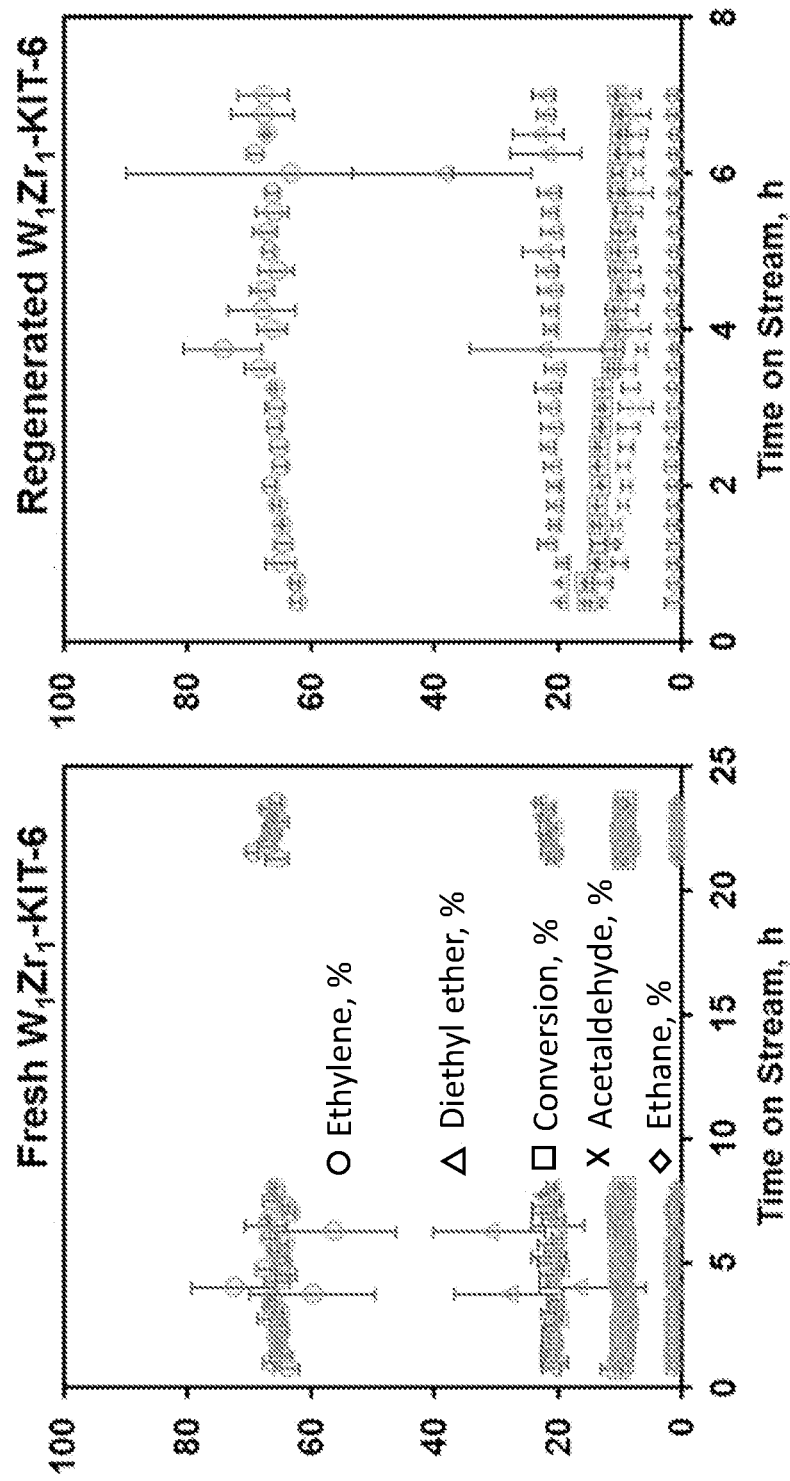
FIGS. 5A-5D show temporal profiles of ethanol conversion and product selectivity on fresh and regenerated catalysts. Operating conditions are listed in Table 4. Fresh and regenerated $W_1Zr_1$-KIT-6 (FIGS. 5A, 5B) and fresh and regenerated $W_{10}Zr_{10}$-KIT-6 (FIGS. 5C, 5D).
Figures 5C, 5D:
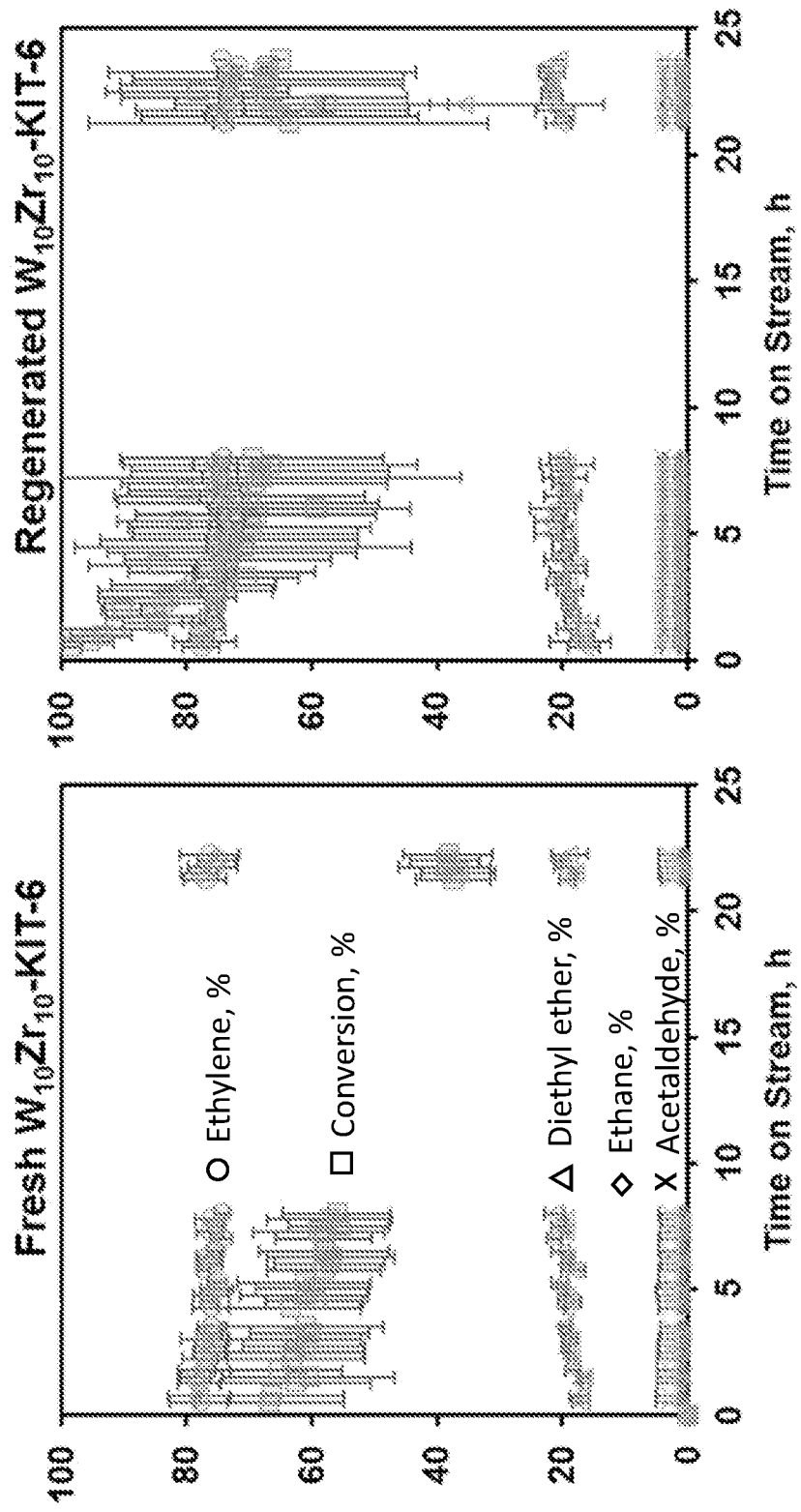

The formations of ethylene and DEE have been generally attributed to the intramolecular and the intermolecular dehydration of ethanol on acid sites, respectively. Also, acid and with metal loading (FIGS. 5A, 5C). The C balances for all experiments closed within 87.2-99.6%. On catalysts with metal loading >6 mol %, lower C balances (≤94%) were observed during the initial 3-5 h, accompanied by the formation of heavy species that were retained in the reactor. While the standard deviation in product yields was <1.3% for a majority of the runs, the deviations were larger on catalysts with the highest metal loading (10 mol % Tables 4 and 5), perhaps due to the increasing complexity of surface structures at such loadings. Similar deviations at higher metal loadings were also observed on Nb-KIT-6 materials.

TABLE 4

Ethanol conversion and product selectivity at early time on stream (0.75-1.5 h)

| $W_xZr_y$ | | $W_0$ | $W_1$ | $W_{2.5}$ | $W_5$ | $W_{10}$ |
|---|---|---|---|---|---|---|
| $Zr_0$ | $X^b$, % | 0.3 | 4.0 | 9.9 | 18.4 | 28.0 ± 8.4 |
| | $C_2H_4^c$, % | 32.8 | 34.7 | 63.4 | 57.3 | 74.7 ± 10.1 |
| | $C_2H_6^c$, % | 0.0 | 4.1 | 2.0 | 1.7 | 1.8 ± 0.2 |
| | $CH_3CHO^c$, % | 66.4 | 45.2 | 22.3 | 13.4 | 6.0 ± 0.3 |
| | $(C_2H_5)_2O^c$, % | 0.8 | 3.6 | 9.8 | 16.3 | 16.6 ± 9.5 |

| | | $W_0$ | $W_1$ | $W_3$ | $W_6$ | $W_{10}$ |
|---|---|---|---|---|---|---|
| $Zr_1$ | $X^b$, % | 4.2 | 14.6 $^a$ | 28.1 | 26.8 | 37.2 |
| | $C_2H_4^c$, % | 26.8 | 62.9 | 71.2 | 73.5 | 72.8 |
| | $C_2H_6^c$, % | 3.8 | 2.5 | 1.2 | 1.2 | 0.9 |
| | $CH_3CHO^c$, % | 42.9 | 10.9 | 4.9 | 4.4 | 4.9 |
| | $(C_2H_5)_2O^c$, % | 13.7 | 20.4 | 21.9 | 20.3 | 20.8 |
| $Zr_{2.5}$ | $X^b$, % | 5.3 | 18.3 | 29.3 $^a$ | 40.3 | 40.8 |
| | $C_2H_4^c$, % | 28.4 | 59.9 | 71.1 | 75.3 | 69.5 |
| | $C_2H_6^c$, % | 4.3 | 2.2 | 0.8 | 0.9 | 0.6 |
| | $CH_3CHO^c$, % | 36.1 | 9.6 | 5.9 | 4.1 | 5.6 |
| | $(C_2H_5)_2O^c$, % | 13.1 | 24.8 | 21.1 | 18.4 | 23.8 |
| $Zr_5$ | $X^b$, % | 8.6 | 17.8 | 30.1 $^a$ | 45.1 $^a$ | 58.9 |
| | $C_2H_4^c$, % | 40.6 | 56.1 | 70.2 | 72.4 | 64.1 |
| | $C_2H_6^c$, % | 2.0 | 2.2 | 0.7 | 0.9 | 0.5 |
| | $CH_3CHO^c$, % | 19.1 | 8.9 | 4.7 | 4.5 | 5.1 |
| | $(C_2H_5)_2O^c$, % | 23.6 | 26.5 | 22.6 | 20.6 | 30.0 |
| $Zr_{10}$ | $X^b$, % | 15.7 | 18.4 | 36.5 | 55.9 | 66.2 ± 11.1 |
| | $C_2H_4^c$, % | 61.6 | 58.5 | 69.5 | 70.2 | 78.0 ± 4.1 |
| | $C_2H_6^c$, % | 0.3 | 1.4 | 0.9 | 0.6 | 1.1 ± 0.4 |
| | $CH_3CHO^c$, % | 5.1 | 8.6 | 7.6 | 4.3 | 2.9 ± 2.0 |
| | $(C_2H_5)_2O^c$, % | 32.5 | 26.9 | 18.6 | 23.5 | 17.2 ± 1.7 |

$^a$ Reproducibility evaluated with 3 experiments, deviation in product yields ≤1.3%, except as noted,
$^b$ Conversion,
$^c$ Product selectivity
Reaction conditions: 330° C., ambient pressure, ethanol WHSV 9.47 h$^{-1}$.

TABLE 5

Ethanol conversion and product selectivity at line-out time on stream (23-24 h)

| $W_xZr_y$ | | $W_0$ | $W_1$ | $W_{2.5}$ | $W_5$ | $W_{10}$ |
|---|---|---|---|---|---|---|
| $Zr_0$ | $X^b$, % | 0.3 | 3.0 | 6.9 | 15.7 | 15.2 ± 5.1 |
| | $C_2H_4$, % | 32.8 | 35.8 | 64.4 | 58.7 | 72.4 ± 7.1 |
| | $C_2H_6$, % | 0.0 | 4.4 | 2.3 | 1.8 | 2.4 ± 0.3 |
| | $CH_3CHO$, % | 66.4 | 45.2 | 22.4 | 14.4 | 8.0 ± 0.4 |
| | $(C_2H_5)_2O$, % | 0.8 | 3.0 | 9.3 | 22.3 | 14.2 ± 7.8 |

| | | $W_0$ | $W_1$ | $W_3$ | $W_6$ | $W_{10}$ |
|---|---|---|---|---|---|---|
| $Zr_1$ | $X^b$, % | 3.4 | 9.5 $^a$ | 23.6 | 13.9 | 23.4 |
| | $C_2H_4^c$, % | 31.1 | 67.6 | 71.9 | 74.8 | 71.4 |
| | $C_2H_6^c$, % | 4.1 | 0.8 | 1.1 | 1.1 | 0.9 |
| | $CH_3CHO^c$, % | 41.0 | 9.9 | 4.7 | 3.8 | 6.8 |
| | $(C_2H_5)_2O^c$, % | 13.5 | 21.6 | 21.7 | 19.6 | 20.3 |
| $Zr_{2.5}$ | $X^b$, % | 4.0 | 16.4 | 23.8 $^a$ | 35.5 | 26.2 |
| | $C_2H_4^c$, % | 30.1 | 62.4 | 75.5 | 75.4 | 64.4 |
| | $C_2H_6^c$, % | 3.4 | 1.9 | 0.5 | 0.8 | 0.6 |
| | $CH_3CHO^c$, % | 22.8 | 8.3 | 3.1 | 4.1 | 5.7 |
| | $(C_2H_5)_2O^c$, % | 24.1 | 25.2 | 20.7 | 18.8 | 23.2 |
| $Zr_5$ | $X^b$, % | 6.7 | 16.2 | 28.9 $^a$ | 33.6 $^a$ | 30.6 |
| | $C_2H_4^c$, % | 59.4 | 58.8 | 70.9 | 70.5 | 59.6 |
| | $C_2H_6^c$, % | 2.4 | 1.8 | 0.5 | 0.8 | 0.5 |
| | $CH_3CHO^c$, % | 7.4 | 7.8 | 4.3 | 4.4 | 6.4 |
| | $(C_2H_5)_2O^c$, % | 28.9 | 27.8 | 23.8 | 20.8 | 22.5 |
| $Zr_{10}$ | $X^b$, % | 11.0 | 14.2 | 24.8 | 43.8 | 38.8 ± 6.3 |
| | $C_2H_4^c$, % | 63.5 | 59.9 | 76.4 | 62.2 | 75.8 ± 4.2 |
| | $C_2H_6^c$, % | 0.3 | 1.3 | 0.7 | 0.4 | 0.8 ± 0.2 |
| | $CH_3CHO^c$, % | 2.8 | 5.3 | 6.7 | 3.7 | 2.8 ± 1.7 |
| | $(C_2H_5)_2O^c$, % | 33.2 | 33.0 | 14.1 | 23.3 | 19.7 ± 1.5 |

$^a$ Reproducibility evaluated with 3 experiments, deviation in product yields ≤0.9%, except as noted,
$^b$ Conversion,
$^c$ Product selectivity
Reaction conditions: 330° C., ambient pressure, ethanol WHSV 9.47 h$^{-1}$.

The ethanol conversion and major product selectivities are summarized in Tables 4 and 5, at time on stream (TOS) around 1 h (average of data points in the 0.75-1.5 h range) and 24 h (average of data points in the 23-24 h range). Under these operating conditions, mass transfer limitations were estimated to be negligible (equations not shown). Both sets of results show that catalyst activity generally increased with metal loading reaching a plateau at W loading ≥6 mol %. The generally higher selectivity towards dehydration products (ethylene+DEE) compared to dehydrogenation product (acetaldehyde) suggests that the acid sites are more dominant than basic sites. To better discern synergistic effects of W and Zr in the $W_xZr_y$-KIT-6 materials, the experimental conversions (bars, FIG. 6) were compared to the sum of corresponding conversions on $W_x$-KIT-6 and $Zr_y$-KIT-6 catalysts at otherwise identical operating conditions (represented by the plane in FIG. 6). The plane was constructed based on interpolated values of conversions on W-KIT-6 and Zr-KIT-6 at intermediate loadings. The extended bars above the planes confirm the positive synergy between W and Zr at certain metal loadings, yielding ethanol conversions that are greater than the sum of the values obtained with monometallic W and Zr catalysts at similar loadings.

The observed synergy on WZr-KIT-6 catalysts may be partially attributed to the strong Brønsted acid sites as revealed by the ssNMR characterization. To probe these sites with a weak base, experiments were performed on spent $W_3Zr_{2.5}$-KIT-6 samples at 300, 330 and 360° C., using either neat ethanol feed or an ethanol feed containing 3.8 mole % acetone, for approximately 24 h to ensure an adequate line-out period. As inferred from Table 6, acetone addition clearly inhibits ethanol dehydration activity on $W_3Zr_{2.5}$-KIT-6 catalyst. This is in sharp contrast to previously reported results wherein acetone addition had a negligible effect on ethanol conversion over Nb-KIT-6 catalysts that possess relatively weak acid sites. The results of Table 4 also suggest that while the acid sites in $W_xZr_y$-KIT-6 are strong enough to interact with acetone, they do not catalyze acetone conversion.

The comparison of W10Zr10-KIT-6 with HZSM-5 and Zeolite Beta is summarized in Table 7. To compare HZSM-5 and W10Zr10-KIT-6 performances at lower ethanol conversions, a lower temperature (300° C.) and higher WHSV (355 $h^{-1}$) were used. Both materials deactivate rapidly and achieve steady ethylene and diethyl ether yields. The lineout TOF (based on the steady yield following the deactivation period) for ethylene formation on HZSM-5 (2.16 mol $g^{-1}h^{-1}$) is approximately 25-fold greater than the TOF observed on $W_{10}Zr_{10}$-KIT-6 (0.085 mol $g^{-1}h^{-1}$). While the initial deactivation is attributed to the rapid formation on and eventual blocking of the strong acid sites by oligomeric byproducts, the remaining activity at line out is attributed to the moderately strong acid sites on both materials. The difference in the activity of these moderately strong sites is possibly due to (a) the lower population of such sites on $W_{10}Zr_{10}$-KIT-6 (0.36 mmol/g) in comparison to that on HZSM-5 (0.64 mmol/g) and (b) the weaker strength of such sites on $W_{10}Zr_{10}$-KIT-6 in comparison to HZSM-5. However, the generation of moderately strong acid sites at all in such metal-incorporated mesoporous silicates is remarkable in comparison to previously reported weakly acidic Zr-KIT-6 (TOF=0.0054 mol $g^{-1}h^{-1}$ at 300° C.) and Nb-KIT-6 (TOF=0.0068 mol $g^{-1}h^{-1}$ at 330° C.). (See Nash, C. P., et al., *Applied Catalysis A: General* 2016, 510, 110-124; and Zhu, H. et al., *AIChE Journal* 2017, 63, 2888-2899.)

Interestingly, at high ethanol WHSV values (9.47 or 355 $h^{-1}$), the potential benefit of enhanced diffusion of fouling species from the $W_{10}Zr_{10}$-KIT-6 mesopores is diminished significantly. In sharp contrast, at the low WHSV of $0.3^{-1}h^{-1}$ typically used in industrial practice, both HZSM-5 and $W_{10}Zr_{10}$-KIT-6 materials achieve total ethanol conversion to ethylene (Table 7). On the basis of the small decrease in ethylene selectivity during the 24 h runs on fresh and regenerated $W_{10}Zr_{10}$-KIT-6 (FIGS. 5C, 5D), the major role of the strong acid sites (in the regenerated sample) appears to be catalyzing the oligomerization reactions rather than ethanol dehydration to ethylene.

TABLE 6

Performance of $W_3Zr_{2.5}$-KIT-6 for ethanol conversion on with/without acetone co-feeding

| Feed | T, ° C. | X, % | Selectivity, % | | | | | |
|---|---|---|---|---|---|---|---|---|
| | | | $C_2H_4$ | $C_2H_6$ | $CH_3CHO$ | $C_4H_8$ | $(CH_3CH_2)_2O$ | Other |
| EtOH | 300 | 15.8 | 53.3 | 0.6 | 9.1 | 0.5 | 36.4 | 0.1 |
| | 330 | 33.0 | 68.1 | 0.5 | 7.3 | 0.7 | 23.3 | 0.1 |
| | 360 | 55.3 | 80.3 | 0.5 | 5.6 | 1.1 | 12.3 | 0.2 |
| EtOH + acetone | 300 | 15.8 | 40.5 | 0.4 | 13.9 | 0.4 | 43.7 | 1.1 |
| | 330 | 29.6 | 57.9 | 0.4 | 9.9 | 0.7 | 24.4 | 6.7 |
| | 360 | 51.7 | 70.8 | 0.4 | 6.7 | 0.9 | 14.0 | 7.1 |

Figure 7:
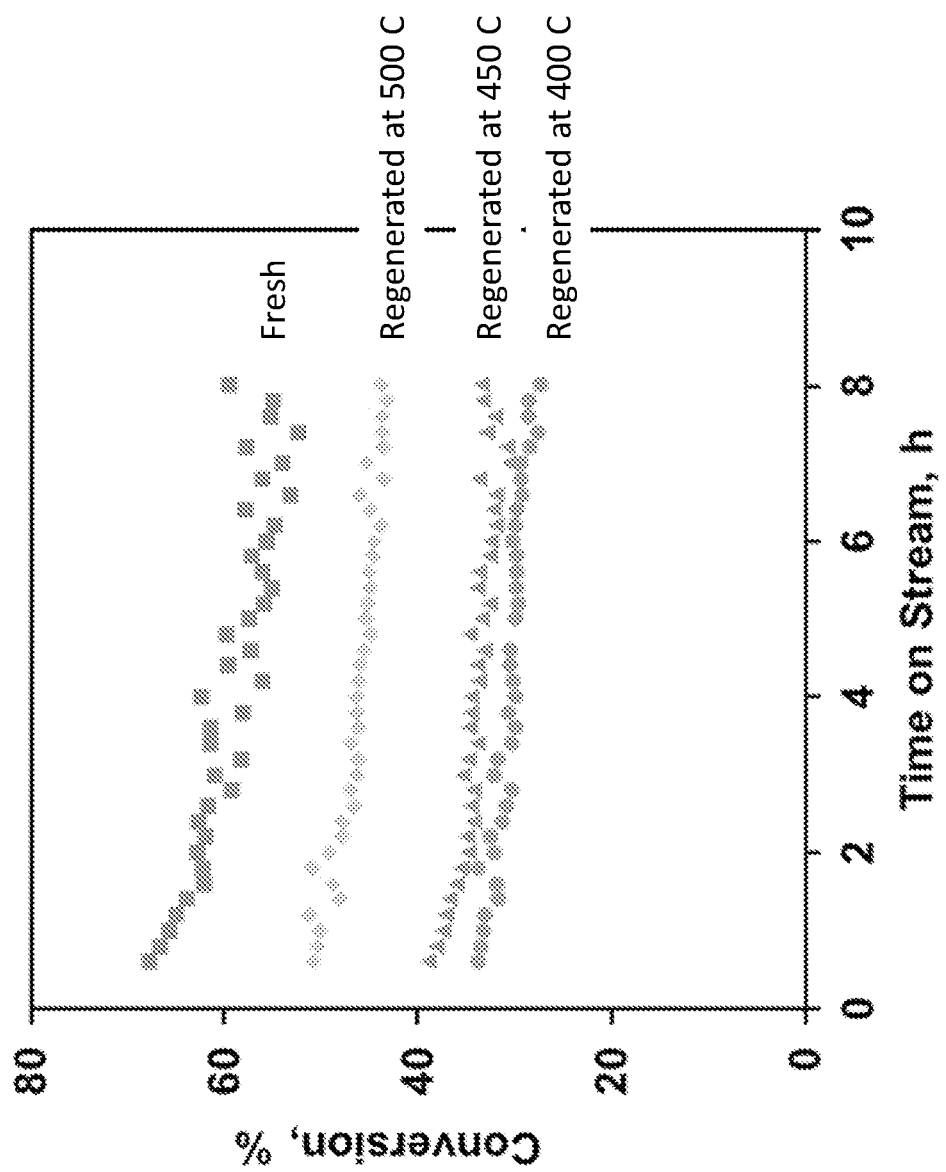
FIG. 7 shows ethanol conversions on a $W_{10}Zr_{10}$-KIT-6 catalyst with post-reaction treatment in nitrogen at various temperatures. Operating conditions are listed in Table 4.

The spent $W_{10}Zr_{10}$-KIT-6 catalyst following a 24 h run was treated in flowing $N_2$ (150 sccm) at 400, 450, 500 and 550° C. for 24 h prior to another run with the pretreated catalyst. The temporal conversion and selectivity profiles in FIG. 7 show that while the $N_2$-treated catalyst partially recovers its original activity at temperatures above 450° C., the activity remains lower than the fresh sample. In contrast, the catalysts regenerated in air show enhanced performance which increased significantly at higher metal loadings. While the regenerated $W_1Zr_1$-KIT-6 shows only a slight increase in activity (FIGS. 5A and 5B), the regenerated $W_{10}Zr_{10}$-KIT-6 exhibits total initial ethanol conversion (FIGS. 5C and 5D). Remarkably, this regeneration process allows the $W_{10}Zr_{10}$-KIT-6 catalyst to perform similarly to HZSM-5 under the same conditions.

TABLE 7

Comparison of $W_{10}Zr_{10}$-KIT-6 with HZSM-5 and Zeolite Beta for Ethanol Dehydration

| Catalyst | WHSV, $h^{-1}$ | T, ° C. | X(EtOH), % | S($C_2H_4$), % | S(DEE), % | TOF, mol $g^{-1}h^{-1}$ |
|---|---|---|---|---|---|---|
| $W_{10}Zr_{10}$-KIT-6 | 1.18 | 330 | ~100 | ~99.3 | 0.1 | |
| HZSM-5 | 1.18 | 330 | ~100 | ~99.7 | 0.0 | |
| Zeolite Beta | 1.18 | 330 | ~100 | ~100 | 0.0 | |
| Fresh $W_{10}Zr_{10}$ | 9.47 | 330 | 66.2 | 78.0 | 17.2 | |

TABLE 7-continued

Comparison of $W_{10}Zr_{10}$-KIT-6 with HZSM-5
and Zeolite Beta for Ethanol Dehydration

| Catalyst | WHSV, $h^{-1}$ | T, °C. | X(EtOH), % | S($C_2H_4$), % | S(DEE), % | TOF, mol $g^{-1}h^{-1}$ |
|---|---|---|---|---|---|---|
| HZSM-5 | 9.47 | 330 | ~100 | ~98.5 | 0.0 | |
| Zeolite Beta | 9.47 | 330 | 78.6 | 75.2 | 20.4 | |
| Regen $W_{10}Zr_{10}$ | 9.47 | 330 | ~100 | 78.4 | 16.6 | |
| $W_{10}Zr_{10}$-KIT-6[a] | 355 | 300 | 1.1 | 41.5 | 56.0 | 0.085 |
| HZSM-5[a] | 355 | 300 | 34.0 | 82.2 | 17.8 | 2.16 |

Figure 8B:
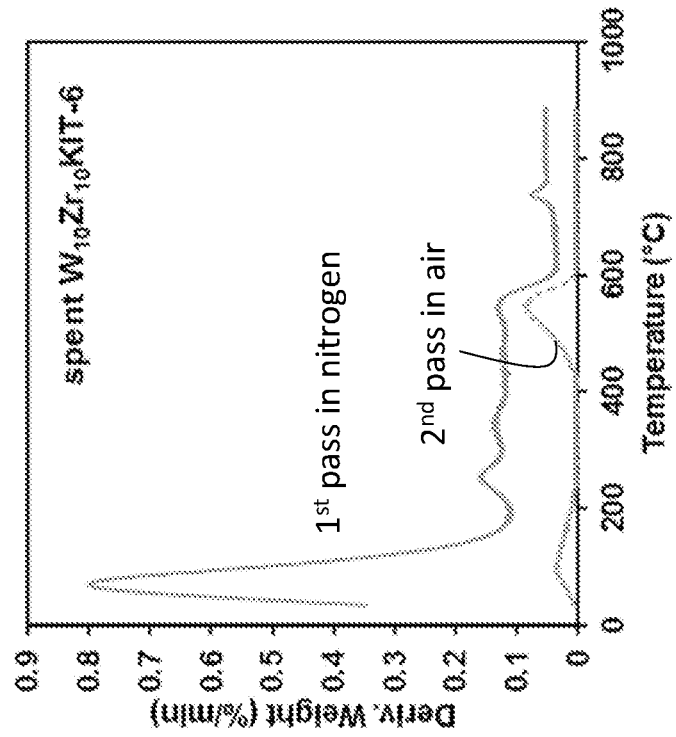
FIGS. 8A-8B show thermogravimetric analysis (TGA) of $W_{10}Zr_{10}$-KIT-6.
Figure 8A:
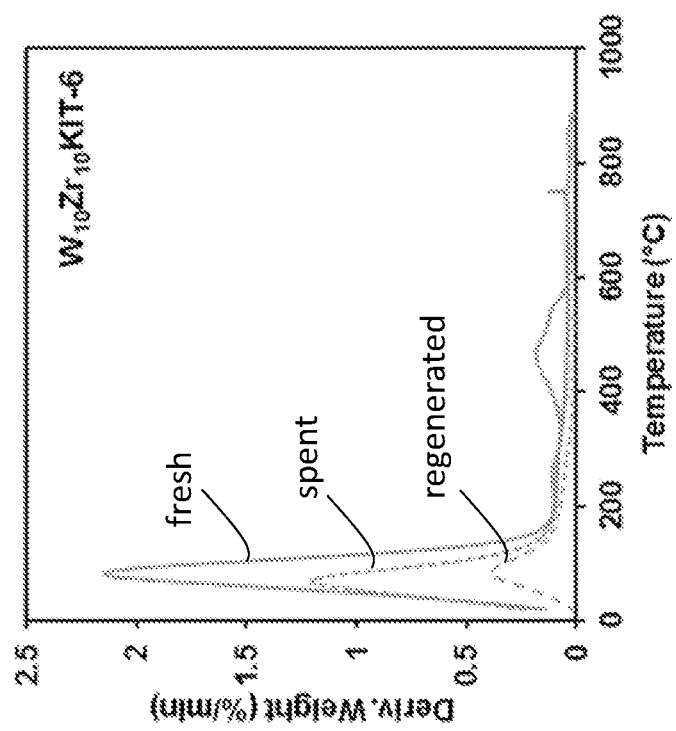

[a]Steady-state results following the rapid deactivation. Reaction conditions: P(EtOH) = 3 kPa Characterization of Spent and Regenerated Catalysts Thermogravimetric analysis of the fresh and the regenerated catalyst samples (FIG. 8A) showed no significant peaks above 200° C. However, the significant change of the peak height around 93° C. suggested that the regenerated catalyst adsorbed less water from the atmosphere, which may be due to changes in the surface sites. Sequential thermogravimetric analysis of a spent sample in flowing nitrogen followed by flowing air (FIG. 8B) showed that the coke formed on the catalyst was not removed in nitrogen even up to 900° C. In contrast, the oligomers and/or coke are completely removed by calcination in air above 550° C.

Figure 9:
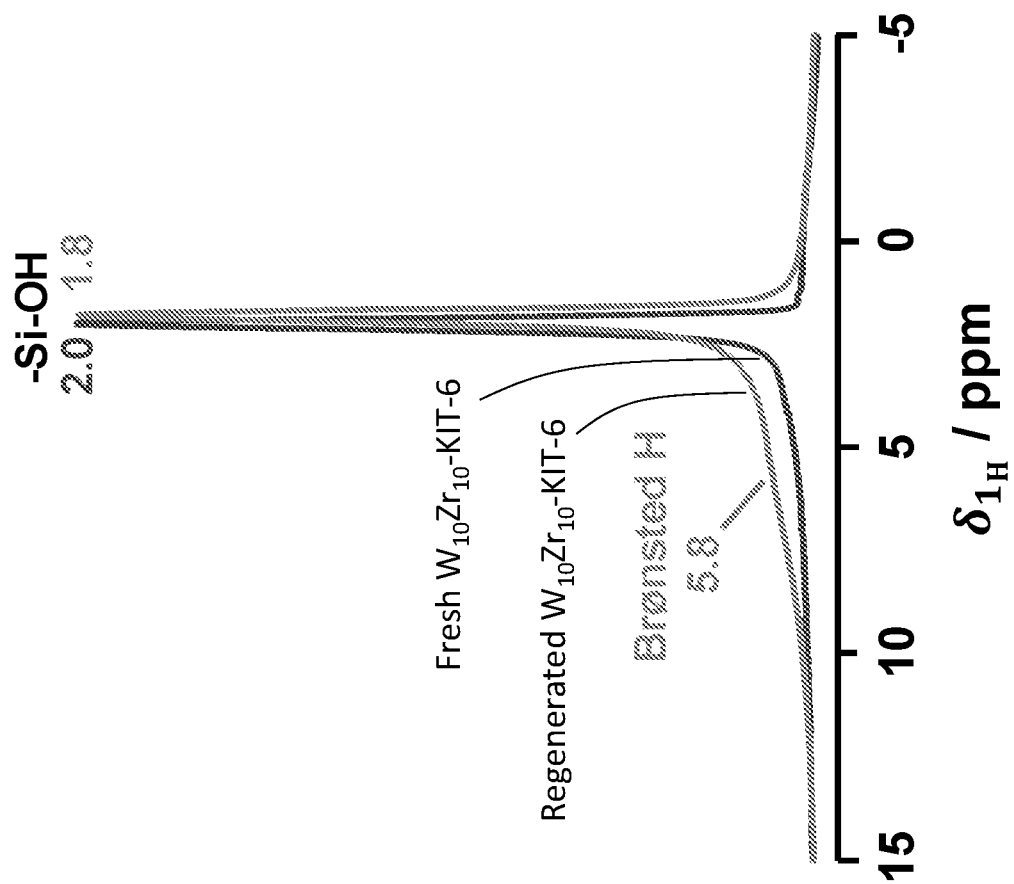
FIG. 9 shows $^1H$ MAS spectra of fresh and air-regenerated catalyst samples.

Solid-state NMR experiments were performed on the regenerated $W_{10}Zr_{10}$-KIT-6 catalyst to investigate the Brønsted acid sites. On the $^1$H MAS spectra of regenerated catalyst (FIG. 9B), the signal around 5.8 ppm clearly intensified compared to the fresh sample (FIG. 9A), suggesting that additional strong Brønsted acid sites are formed during reaction and/or regeneration. Such chemical shifts suggest that the strength of the generated Brønsted acid sites is comparable to the bridging Brønsted acid sites [Si(OH)Al] on H-ZSM-5, H—Y or H-MOR zeolites. However, the samples adsorbed with pyridine-$d_5$ under a dry argon environment showed spectra similar to those of the fresh samples, suggesting that the strong Brønsted acid sites are probably inaccessible by pyridine (data not shown).

Solid-state NMR spectra following pyridine adsorption reveal three general types of acidic protons on the fresh and regenerated $W_{10}Zr_{10}$-KIT-6 materials: (a) metal hydroxyl groups with possible hydrogen bonding that exhibit weak acidity similar to that of silanol, (b) moderately acidic protons possibly bound to structures with small-scale electron delocalization, (c) pyridine-inaccessible strongly acidic protons generated after regeneration. The EDX elemental mapping (data not shown) reveals the proximate distribution of W and Zr species on $W_{10}Zr_{10}$KIT-6, suggesting that W—O—Zr clusters isolated by Si exist on the material. Statistically, such a cluster has a higher formation probability during the synthesis of the $W_xZr_y$-KIT-6 catalysts with higher W and Zr metal loadings that show higher ethanol dehydration activity. Using the NW Chem 6.8-47 package, computational $^1$H NMR results (data not shown) show that the proton of the metal hydroxyl group on an isolated W—O—Zr cluster matches the experimental $^1$H ssNMR chemical shift in the 3-4 ppm range on the fresh $W_xZr_y$-KIT-6. Interestingly, the relatively narrow band gaps of $WO_3$ (2.5-3.2 eV) and $ZrO_2$ (5-6 eV) in comparison to amorphous $SiO_2$ (~9 eV) suggest that well-delocalized orbitals may occur in a chain of -(M-O)$_n$— (M=Zr, W) which could increase proton activity in comparison to structures wherein the delocalization could be cut off by Si atoms. Such structures including 3D polytungstate cages or polytungstate networks with Zr substitution may exist on the $W_xZr_y$-KIT-6 materials and host the strong acidic protons, aided by a Keggin-type anion in ammonium metatungstate, the W source. The strong Brønsted acid sites possibly reside in structures with relatively long-range electron delocalization such as self-assembled monotungstate with Zr substitution (data not shown). Indeed, DFT results confirmed that the deprotonation energy is decreased in W-heteropolyacids (1089-1060 kJ/mol) in comparison to Zr—O(H)—W(=O)$_2$—O—Zr clusters on $WO_x/ZrO_2$. Such assignments of acidic protons observed by ssNMR are also consistent with the acid strength order, zeolite <$WO_x/ZrO_2$<W-heteropoly acids. More interestingly, such cage structures may contain central protons which may be related to the protons inaccessible to pyridine, as observed in the ssNMR spectra (data not shown). On $W_xZr_y$-KIT-6 materials, the Si atoms not only serve as backbones for the mesoporous framework but also decrease the formation of large heteropolytungstate structures with even stronger acidity that will possibly catalyze undesired side reactions that cause deactivation.

Brønsted acid sites may be generated in the presence of water during alcohol dehydration on tungstated zirconia3 and niobia. Despite the significant increase in strong Brønsted acid sites, the amount of acid sites measured by $NH_3$-TPD on the regenerated catalyst was almost unchanged (0.56 mmol $NH_3$/g) in comparison to a fresh sample (0.58 mmol $NH_3$/g), suggesting that the $NH_3$ adsorbed on the strong acid sites does not desorb below 550° C. Lewis acid sites may be converted to Brønsted acid sites via dissociative adsorption of water. In addition, on the basis of the DRIFT spectra of the pyridine adsorbed samples, the approximate Lewis/Brønsted acid ratio was estimated to decrease from 1.22 on fresh catalyst to 0.43 on the regenerated catalyst. Nitrogen sorption revealed only a small decrease in specific surface area (525 to 503 m$^2$/g) and pore volume (0.75 to 0.72 cm$^3$/g), indicating good thermal stability of the material during the 24 h run. These characterizations further confirm that the activity enhancement in the regenerated catalysts is related to changes in the surface acid sites rather than changes in textural properties. Without wishing to be bound to any theory, the observations suggest that the generation of the Brønsted acid sites is related to the formation of heteropolytungstate as well as the water addition onto the structure. Both of these pathways can be promoted by the water and free radicals generated from combustion of the hydrocarbon species deposited on the catalyst surface. The dissociated water molecules are relatively strongly bound, possibly in remote locations on a heteropolytungstate network.

CONCLUSIONS

This Example has shown that strong Brønsted acid sites that are comparable in strength to those found in zeolites (HZSM-5, HY and HMOR) may be formed by the incorporation of various amounts (up to 10 mol %) of W and Zr species into the ordered mesoporous KIT-6 framework via a one-pot synthesis. The WZr-KIT-6 catalysts display tunable Lewis and Brønsted acidity based on metal loadings, retaining mesoporosity with relatively large surface areas (438-980 m$^2$/g) and pore volumes (0.61-1.65 cm$^3$/g). Multiple types of Lewis and Brønsted acid sites were observed via ssNMR characterization, including new Lewis sites (possibly metal center in W—O—Zr structure) and strong Brønsted sites which are present only on the regenerated bimetallic WZr-KIT-6 formulations and not on either W-KIT-6 or Zr-KIT-6 materials. On the basis of ssNMR analysis, the moderately strong Brønsted acid sites present on the fresh WZr-KIT-6 material are assigned to the acidic protons of the hydroxyl groups bound to the metals in W—O—Zr structures. These new acid sites could be responsible for the enhanced performance of WZr-KIT-6 for ethanol dehydration compared to either W-KIT-6 or Zr-KIT-6. The enhanced selectivity towards ethylene and DEE on WZr-KIT-6 materials imply that the products form mainly from acid sites and less from basic sites. The presence of strong Brønsted acid sites in WZr-KIT-6 materials was also confirmed when co-feeding acetone (a weak base) significantly depresses ethanol dehydration activity. Temporal ethanol conversion profiles on WZr-KIT-6 catalysts show a gradual deactivation trend possibly due to coverage of the acid sites by oligomers and/or coke. Air-regenerated WZr-KIT-6 catalysts with high metal loadings not only revealed good stability during 24 h runs, but also exhibited exceptionally higher activity than a fresh catalyst. This enhancement is due to the generation of additional strong Brønsted acid sites during the dehydration reaction and/or regeneration in flowing air. These strong Brønsted acid sites are attributed to the protons on heteropolytungstate structures formed from the water and free radicals generated during coke combustion. These results show that WZr-KIT-6 materials find applications in reactions that require strong Brønsted acid sites and can benefit from the presence of mesopores to inhibit catalyst deactivation by fouling.

Additional detail and experimental results, including the data not shown above, may be found in U.S. Prov. Pat. Application No. 62/621,691, which is hereby incorporated by reference in its entirety.

The word "illustrative" is used herein to mean serving as an example, instance, or illustration. Any aspect or design described herein as "illustrative" is not necessarily to be construed as preferred or advantageous over other aspects or designs. Further, for the purposes of this disclosure and unless otherwise specified, "a" or "an" means "one or more."

The foregoing description of illustrative embodiments of the disclosure has been presented for purposes of illustration and of description. It is not intended to be exhaustive or to limit the disclosure to the precise form disclosed, and modifications and variations are possible in light of the above teachings or may be acquired from practice of the disclosure. The embodiments were chosen and described in order to explain the principles of the disclosure and as practical applications of the invention to enable one skilled in the art to utilize the invention in various embodiments and with various modifications as suited to the particular use contemplated. It is intended that the scope of the disclosure be defined by the claims appended hereto and their equivalents.

What is claimed is:

1. A bimetal-incorporated mesoporous silicate catalyst, the catalyst comprising a silicate lattice, a first transition metal M, and a second transition metal M', wherein M and M' are selected from Zr and W and are directly incorporated into the silicate lattice such that M and M' replace Si atoms, wherein the catalyst is W$_x$Zr$_y$-KIT-6 or W$_x$Zr$_y$-KIT-5 or a mixture thereof and x and y are non-zero.

2. The catalyst of claim 1, wherein the catalyst comprises Brønsted acid sites corresponding to protons of hydroxyl groups bound to M, M', or both, of a M-O-M' species, or a cluster of M-O-M' species, in the catalyst.

3. The catalyst of claim 1, wherein the catalyst comprises Brønsted acid sites exhibiting a proton shift of at least 4.7 ppm in $^1$H magic angle spinning (MAS) NMR.

4. The catalyst of claim 2, wherein the catalyst further comprises Lewis acid sites corresponding to M, M', or both, of the M-O-M' species, or the cluster of M-O-M' species, in the catalyst.

5. The catalyst of claim 2, wherein the catalyst further comprises Lewis acid sites exhibiting a pyridinium signal of no more than 261 ppm in $^{15}$N cross-polarization (CP) MAS NMR.

6. The catalyst of claim 1, wherein the catalyst comprises Brønsted acid sites corresponding to protons bound to oxygen in a heteropolymeric network of M, M', and O in the catalyst.

7. The catalyst of claim 6, wherein one of M and M' is W and the heteropolymeric network is a heteropolytungstate network.

8. The catalyst of claim 6, wherein the catalyst comprises Brønsted acid sites exhibiting a proton shift of at least 5.8 ppm in $^1$H MAS NMR.

9. The catalyst of claim 1, wherein x and y are each in a range of greater than zero to 10.

10. The catalyst of claim 1, wherein the catalyst is W$_3$Zr$_{2.5}$-KIT-6, W$_3$Zr$_{2.5}$-KIT-5, W$_{10}$Zr$_{10}$-KIT-6, W$_{10}$Zr$_{10}$-KIT-5, or a mixture thereof.

11. A method of dehydrating an alcohol, the method comprising exposing an alcohol to the catalyst of claim 1 in a reactor under conditions sufficient to dehydrate the alcohol to one or more dehydration products.

12. A method of making a bimetal-incorporated mesoporous silicate catalyst, the method comprising:
exposing a coke-contaminated bimetal-incorporated mesoporous silicate catalyst to air at an elevated temperature and for a period of time, the catalyst comprising coke on its surface and a silicate lattice, a first transition metal M, and a second transition metal M', wherein M and M' are selected from Zr and W and are directly incorporated into the silicate lattice such that M and M' replace Si atoms, wherein the catalyst is W$_x$Zr$_y$-KIT-6 or W$_x$Zr$_y$-KIT-5 or a mixture thereof and x and y are non-zero, to form a bimetal-incorporated mesoporous silicate catalyst comprising Brønsted acid sites having a strength greater than those of the coke-contaminated catalyst.

13. The method of claim 12, wherein the bimetal-incorporated mesoporous silicate catalyst comprises Brønsted acid sites corresponding to protons bound to oxygen in a heteropolymeric network of M, M', and O in the catalyst.

14. The method of claim 13, wherein one of M and M' is W and the heteropolymeric network is a heteropolytungstate network.

* * * * *